US010688153B2

(12) United States Patent
Vanden Hoek et al.

(10) Patent No.: US 10,688,153 B2
(45) Date of Patent: Jun. 23, 2020

(54) PEPTIDES AND METHOD FOR TREATMENT OF CARDIAC ARREST

(71) Applicant: THE BOARD OF TRUSTEES OF THE UNIVERSITY OF ILLINOIS, Urbana, IL (US)

(72) Inventors: Terry Vanden Hoek, Chicago, IL (US); Xiangdong Zhu, Chicago, IL (US); Jing Li, Chicago, IL (US)

(73) Assignee: The Board of Trustees of the University of Illinois, Urbaba, IL (US)

( * ) Notice: Subject to any disclaimer, the term of this patent is extended or adjusted under 35 U.S.C. 154(b) by 0 days.

(21) Appl. No.: 15/769,132

(22) PCT Filed: Nov. 7, 2016

(86) PCT No.: PCT/US2016/060789
§ 371 (c)(1),
(2) Date: Apr. 18, 2018

(87) PCT Pub. No.: WO2017/079725
PCT Pub. Date: May 11, 2017

(65) Prior Publication Data
US 2018/0296640 A1 Oct. 18, 2018

Related U.S. Application Data

(60) Provisional application No. 62/252,201, filed on Nov. 6, 2015.

(51) Int. Cl.
| | |
|---|---|
| *A61K 38/16* | (2006.01) |
| *A61K 38/10* | (2006.01) |
| *A61K 38/08* | (2019.01) |
| *A61K 38/00* | (2006.01) |
| *A61P 9/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 38/04* | (2006.01) |
| *A61K 38/17* | (2006.01) |
| *C40B 40/08* | (2006.01) |
| *G01N 33/68* | (2006.01) |
| *C12N 5/10* | (2006.01) |
| *C12N 9/16* | (2006.01) |
| *C12N 9/12* | (2006.01) |
| *A61P 9/04* | (2006.01) |
| *A61K 31/455* | (2006.01) |

(52) U.S. Cl.
CPC ............ *A61K 38/1761* (2013.01); *A61P 9/04* (2018.01); *C07K 16/00* (2013.01); *C12N 5/10* (2013.01); *C12N 9/1205* (2013.01); *C12N 9/16* (2013.01); *C40B 40/08* (2013.01); *G01N 33/6893* (2013.01); *A61K 31/455* (2013.01); *A61K 2300/00* (2013.01); *C07K 2319/00* (2013.01); *C12Y 301/03016* (2013.01); *G01N 2800/325* (2013.01); *G01N 2800/52* (2013.01)

(58) Field of Classification Search
CPC .............. A61K 2300/00; A61K 31/455; A61K 38/1761; A61P 9/04; C07K 16/00; C07K 2319/00
See application file for complete search history.

(56) References Cited

U.S. PATENT DOCUMENTS

| | | | |
|---|---|---|---|
| 2007/0196883 A1 | 8/2007 | Alessi et al. ..................... 435/15 |
| 2008/0108569 A1 | 5/2008 | Newton et al. ............... 514/18.9 |
| 2009/0269796 A1 | 10/2009 | Gerszten et al. ............... 435/29 |
| 2014/0323406 A1 | 10/2014 | Tymianksi .................... 514/15.1 |
| 2014/0371161 A1* | 12/2014 | Koeberle ............... C07K 14/71 |
| | | | 514/20.8 |

FOREIGN PATENT DOCUMENTS

| | | |
|---|---|---|
| CN | 201210382244 | 10/2012 |
| WO | 2008/014917 | 2/2008 |
| WO | 2012/092323 | 7/2012 |
| WO | 2015/006830 | 1/2015 |

OTHER PUBLICATIONS

Anonymous "PH domain leucine-rich repeat-containing protein phophatase 1" https://www.phosphosite.org/proteinAction?id=8238&showAllSites=true#appletMsg (Year: 2019).*
Jackon et al. "Detection of PHLPP1a/b in Human and Mouse Brain by Different Anti-PHLPP1 Antibodies" Scientific Reports 5:9377 (Year: 2015).*
Zhu et al. "Abstract 17773: Peptide Inhibition of PTEN Increases Mouse Survival after Sudden Cardiac Arrest" Circulations 130: A17773 (Year: 2014).*
Klaidman et al. "Nicotinamide Offers Multiple Protecting Mechanisms in Stroke as a Precursor for NAD, as a PARP Inhibitor and by Partial Restoration of Mitochondrial Function" Pharmacology 69:150-157 (Year: 2003).*
Miyamoto et al. "PHLPP-1 Negatively Regulates Akt Activity and Survival in the Heart" Circ. Res. 107:476-484. (Year: 2010).*
Warfel N and Newton A "Pleckstrin Homology Domain Leucine-rich Repeat Protein Phosphatase (PHLPP): A New Player in Cell Signaling" J. Biol. Chem. 6:3610-3616. (Year: 2012).*

(Continued)

*Primary Examiner* — Christina Bradley
*Assistant Examiner* — Zachary J Miknis
(74) *Attorney, Agent, or Firm* — Licata & Tyrrell P.C.

(57) ABSTRACT

Modified peptides based on C-terminal PDZ binding domains of PTEN and PHLPP, or PDK1 interacting fragment of PKN2 are described as are methods of using the modified peptides for blocking the activity of PTEN, PHLPP and PKN2 and treating sudden cardiac arrest. A method for guiding treatment of cardiac arrest based on sorbitol or taurine levels is also provided.

9 Claims, 3 Drawing Sheets

Specification includes a Sequence Listing.

(56) References Cited

OTHER PUBLICATIONS

Balendran et al "PDK1 acquires PDK2 activity in the presence of a synthetic peptide derived from the carboxyl terminus of PRK2" Curr. Biol. 1999 9:393-404.

Gao et al "PHLPP: a phosphatase that directly dephosphorylates Akt, promotes apoptosis, and suppresses tumor growth" Mol. Cell 2005 18:13-24.

Gee et al "Single-amino acid substitutions alter the specificity and affinity of PDZ domains for their ligands" Biochemistry 2000 39:14638-14646.

Jackson et al "Detection of PHLPP1α/β in human and mouse brain by different anti-PHLPP1 antibodies" Sci. Rep. 2015 5:1-8.

Li et al "A novel pharmacological strategy by PTEN inhibition for improving metabolic resuscitation and survival after mouse cardiac arrest" Am. J. Physiol. Heart Circ. Physiol. 2015 308:H1414-H1422.

Miyamoto et al "PHLPP-1 negatively regulates Akt activity and survival in the heart" Circ. Res. 2010 107:476-484.

Ruan et al "Inducible and cardiac specific PTEN inactivation protects ischemia/reperfusion injury" J. Mol. Cell Cardiol. 2009 46:193-200.

Schwartzbauer & Robbins "The tumor suppressor gene PTEN can regulate cardiac hypertrophy and survival" J. Biol. Chem. 2001 276:35786-35793.

Zhu et al "TAT-protein blockade during ischemia/reperfusion reveals critical role for p85 PI3K-PTEN interaction in cardiomyocyte injury" *PLoS One* 2014 9:1-8.

International Search Report and Written Opinion in PCT/US2016/060789 dated Mar. 31, 2017.

International Preliminary Report on Patentability in PCT/US2016/060789 dated May 17, 2018.

\* cited by examiner

SEQUENCE LISTING

```
<160> NUMBER OF SEQ ID NOS: 208

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa denotes Ser or Thr

<400> SEQUENCE: 1

Asx Gln His Xaa Gln Ile Thr Lys Val
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa denotes Cys or Tyr

<400> SEQUENCE: 2

Leu Pro Asx Xaa Tyr Asx Thr Pro Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Arg or His
<220> FEATURE:
<221> NAME/KEY: MISC_FEATURE
<222> LOCATION: (7)..(7)
<223> OTHER INFORMATION: Xaa denotes Ile or Val

<400> SEQUENCE: 3

Phe Xaa Asx Phe Asx Tyr Xaa Ala Asx
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4
```

Asp Gln His Ser Gln Ile Thr Lys Val
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Asp Gln His Thr Gln Ile Thr Lys Val
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Asn Gln His Ser Gln Ile Thr Lys Val
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Asn Gln His Thr Gln Ile Thr Lys Val
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Leu Pro Asp Cys Tyr Asp Thr Pro Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Leu Pro Asp Tyr Tyr Asp Thr Pro Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

```
Leu Pro Asn Cys Tyr Asp Thr Pro Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Leu Pro Asn Tyr Tyr Asp Thr Pro Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Leu Pro Asp Cys Tyr Asn Thr Pro Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Leu Pro Asp Tyr Tyr Asn Thr Pro Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Leu Pro Asn Cys Tyr Asn Thr Pro Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Leu Pro Asn Tyr Tyr Asn Thr Pro Leu
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Phe His Asp Phe Asp Tyr Val Ala Asp
```

```
1               5
```

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

```
Phe Arg Asp Phe Asp Tyr Ile Ala Asp
1               5
```

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

```
Phe His Asn Phe Asp Tyr Val Ala Asp
1               5
```

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

```
Phe Arg Asn Phe Asp Tyr Ile Ala Asp
1               5
```

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

```
Phe His Asp Phe Asn Tyr Val Ala Asp
1               5
```

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

```
Phe Arg Asp Phe Asn Tyr Ile Ala Asp
1               5
```

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

```
Phe His Asp Phe Asp Tyr Val Ala Asn
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Phe Arg Asp Phe Asp Tyr Ile Ala Asn
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Phe His Asn Phe Asn Tyr Val Ala Asp
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Phe Arg Asn Phe Asn Tyr Ile Ala Asp
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Phe His Asn Phe Asp Tyr Val Ala Asn
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Phe Arg Asn Phe Asp Tyr Ile Ala Asn
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Phe His Asp Phe Asn Tyr Val Ala Asn
1               5
```

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

Phe Arg Asp Phe Asn Tyr Ile Ala Asn
1               5

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Asn Glu Pro Phe Asp Glu Asp Gln His Thr Gln Ile Thr Lys Val
1               5                   10                  15

<210> SEQ ID NO 31
<211> LENGTH: 18
<212> TYPE: PRT
<213> ORGANISM: Artificial Sequence
<220> FEATURE:
<223> OTHER INFORMATION: Synthetic peptide

<400> SEQUENCE: 31

Lys Leu Ala Leu Lys Leu Ala Leu Lys Ala Leu Lys Ala Ala Leu Lys
1               5                   10                  15

Leu Ala

<210> SEQ ID NO 32
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is present or absent and when present
      denotes Lys or Val
<220> FEATURE:
<221> NAME/KEY: MISC_FEATURE
<222> LOCATION: (2)..(2)
<223> OTHER INFORMATION: Xaa is present or absent and when present
      denotes Lys
<220> FEATURE:
<221> NAME/KEY: MISC_FEATURE
<222> LOCATION: (8)..(8)
<223> OTHER INFORMATION: Xaa denotes any amino acid residue
<220> FEATURE:
<221> NAME/KEY: MISC_FEATURE
<222> LOCATION: (11)..(11)
<223> OTHER INFORMATION: Xaa is present or absent and when present
      denotes Lys
<220> FEATURE:
<221> NAME/KEY: MISC_FEATURE
<222> LOCATION: (12)..(12)
<223> OTHER INFORMATION: Xaa is present or absent and when present
      denotes Ile
<220> FEATURE:
<221> NAME/KEY: MISC_FEATURE
<222> LOCATION: (13)..(16)
<223> OTHER INFORMATION: Xaa is present or absent and when present
      denotes any amino acid residue

<400> SEQUENCE: 32

```
Xaa Xaa Lys Lys Lys Ile Lys Xaa Glu Ile Xaa Xaa Xaa Xaa Xaa
1               5                   10                  15
```

<210> SEQ ID NO 33
<211> LENGTH: 12
<212> TYPE: PRT
<213> ORGANISM: Artificial Sequence
<220> FEATURE:
<223> OTHER INFORMATION: Synthetic peptide

<400> SEQUENCE: 33

```
Val Lys Lys Lys Lys Ile Lys Arg Glu Ile Lys Ile
1               5                   10
```

<210> SEQ ID NO 34
<211> LENGTH: 12
<212> TYPE: PRT
<213> ORGANISM: Artificial Sequence
<220> FEATURE:
<223> OTHER INFORMATION: Synthetic peptide

<400> SEQUENCE: 34

```
Val Lys Lys Lys Lys Ile Lys Asn Glu Ile Lys Ile
1               5                   10
```

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide

<400> SEQUENCE: 35

```
Val Lys Lys Lys Lys Ile Lys Ala Glu Ile Lys Ile
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: Synthetic peptide

<400> SEQUENCE: 36

```
Val Lys Lys Lys Lys Ile Lys Lys Glu Ile Lys Ile
1               5                   10
```

<210> SEQ ID NO 37
<211> LENGTH: 18
<212> TYPE: PRT
<213> ORGANISM: Artificial Sequence
<220> FEATURE:
<223> OTHER INFORMATION: Synthetic peptide

<400> SEQUENCE: 37

```
Arg Gln Lys Arg Leu Ile Arg Gln Lys Arg Leu Ile Arg Gln Lys Arg
1               5                   10                  15

Leu Ile
```

<210> SEQ ID NO 38
<211> LENGTH: 18
<212> TYPE: PRT
<213> ORGANISM: Artificial Sequence
<220> FEATURE:
<223> OTHER INFORMATION: Synthetic peptide

```
<400> SEQUENCE: 38

Arg His Ser Arg Ile Gly Arg His Ser Arg Ile Gly Arg His Ser Arg
1               5                   10                  15

Ile Gly

<210> SEQ ID NO 39
<211> LENGTH: 16
<212> TYPE: PRT
<213> ORGANISM: Artificial Sequence
<220> FEATURE:
<223> OTHER INFORMATION: Synthetic peptide

<400> SEQUENCE: 39

Arg His Ser Arg Ile Gly Ile Ile Gln Gln Arg Arg Thr Arg Asn Gly
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Synthetic peptide

<400> SEQUENCE: 40

Arg His Ser Arg Ile Gly Val Thr Arg Gln Arg Arg Ala Arg Asn Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic peptide

<400> SEQUENCE: 41

Arg Arg Arg Arg Arg Arg Arg Ser Arg Gly Arg Arg Arg Thr Tyr
1               5                   10                  15

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Arg Lys Lys Arg Arg Gln Arg Arg Arg
1               5

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide

<400> SEQUENCE: 43

Tyr Gly Arg Lys Lys Arg Arg Gln Arg Arg Arg
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 44

Arg Arg Arg Arg Arg Arg Arg Arg
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic peptide

<400> SEQUENCE: 45

Arg Arg Arg Arg Arg Arg Arg Arg Arg Arg
1               5                   10

<210> SEQ ID NO 46
<211> LENGTH: 32
<212> TYPE: PRT
<213> ORGANISM: Artificial Sequence
<220> FEATURE:
<223> OTHER INFORMATION: Synthetic peptide

<400> SEQUENCE: 46

Gly Leu Phe Glu Ala Ile Glu Gly Phe Ile Glu Asn Gly Trp Glu Gly
1               5                   10                  15

Met Ile Asp Gly Trp Tyr Gly Arg Arg Arg Arg Arg Arg Arg Arg
            20                  25                  30

<210> SEQ ID NO 47
<211> LENGTH: 16
<212> TYPE: PRT
<213> ORGANISM: Artificial Sequence
<220> FEATURE:
<223> OTHER INFORMATION: Synthetic peptide

<400> SEQUENCE: 47

Arg Gln Ile Lys Ile Trp Phe Gln Asn Arg Arg Met Lys Trp Lys Lys
1               5                   10                  15

<210> SEQ ID NO 48
<211> LENGTH: 27
<212> TYPE: PRT
<213> ORGANISM: Artificial Sequence
<220> FEATURE:
<223> OTHER INFORMATION: Synthetic peptide

<400> SEQUENCE: 48

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 49
<211> LENGTH: 33
<212> TYPE: PRT
<213> ORGANISM: Artificial Sequence
<220> FEATURE:
<223> OTHER INFORMATION: Synthetic peptide

<400> SEQUENCE: 49

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30
```

Arg

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide

<400> SEQUENCE: 50

Lys Lys Lys Lys Lys Lys Lys Lys Lys Lys
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Lys Lys Lys Lys Lys Lys Lys Lys Lys
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic peptide

<400> SEQUENCE: 52

Tyr Ala Arg Ala Ala Ala Arg Gln Ala Arg Ala
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic peptide

<400> SEQUENCE: 53

Pro Leu Ser Ser Ile Phe Ser Arg Ile Gly Asp Pro
1               5                   10

<210> SEQ ID NO 54
<211> LENGTH: 27
<212> TYPE: PRT
<213> ORGANISM: Artificial Sequence
<220> FEATURE:
<223> OTHER INFORMATION: Synthetic peptide

<400> SEQUENCE: 54

Met Ala Asn Leu Gly Tyr Trp Leu Leu Ala Leu Phe Val Met Trp Thr
1               5                   10                  15

Asp Val Gly Leu Cys Lys Lys Arg Pro Lys Pro
            20                  25

<210> SEQ ID NO 55
<211> LENGTH: 35
<212> TYPE: PRT
<213> ORGANISM: Artificial Sequence
<220> FEATURE:
<223> OTHER INFORMATION: Synthetic peptide

```
<400> SEQUENCE: 55

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala
        35

<210> SEQ ID NO 56
<211> LENGTH: 19
<212> TYPE: PRT
<213> ORGANISM: Artificial Sequence
<220> FEATURE:
<223> OTHER INFORMATION: Synthetic peptide

<400> SEQUENCE: 56

Leu Leu Ile Ile Leu Arg Arg Arg Arg Ile Arg Lys Gln Ala His Ala
1               5                   10                  15

His Ser Lys

<210> SEQ ID NO 57
<211> LENGTH: 23
<212> TYPE: PRT
<213> ORGANISM: Artificial Sequence
<220> FEATURE:
<223> OTHER INFORMATION: Synthetic peptide

<400> SEQUENCE: 57

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 58
<211> LENGTH: 22
<212> TYPE: PRT
<213> ORGANISM: Artificial Sequence
<220> FEATURE:
<223> OTHER INFORMATION: Synthetic peptide

<400> SEQUENCE: 58

Thr Pro Trp Trp Arg Leu Trp Thr Lys Trp His His Lys Arg Arg Asp
1               5                   10                  15

Leu Pro Arg Lys Pro Glu
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic peptide

<400> SEQUENCE: 59

Gly Leu Trp Arg Ala Leu Trp Arg Leu Leu Arg Ser Leu Trp Arg Leu
1               5                   10                  15

Leu Trp Arg Ala
            20

<210> SEQ ID NO 60
<211> LENGTH: 23
<212> TYPE: PRT
<213> ORGANISM: Artificial Sequence
```

<220> FEATURE:
<223> OTHER INFORMATION: Synthetic peptide

<400> SEQUENCE: 60

Asp Ser His Ala Lys Arg His His Gly Tyr Arg Lys Phe His Glu Lys
1               5                   10                  15

His His Ser His Arg Gly Tyr
            20

<210> SEQ ID NO 61
<211> LENGTH: 16
<212> TYPE: PRT
<213> ORGANISM: Artificial Sequence
<220> FEATURE:
<223> OTHER INFORMATION: Synthetic peptide

<400> SEQUENCE: 61

Lys Lys Lys Glu Glu Arg Ala Asp Leu Ile Ala Tyr Leu Lys Lys Ala
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic peptide

<400> SEQUENCE: 62

Gly Leu Arg Lys Arg Leu Arg Lys Phe Arg Asn Lys Ile Lys Glu Lys
1               5                   10                  15

<210> SEQ ID NO 63
<211> LENGTH: 20
<212> TYPE: PRT
<213> ORGANISM: Artificial Sequence
<220> FEATURE:
<223> OTHER INFORMATION: Synthetic peptide

<400> SEQUENCE: 63

Tyr Gly Arg Lys Lys Arg Arg Gln Arg Arg Arg Leu Pro Asp Cys Tyr
1               5                   10                  15

Asp Thr Pro Leu
            20

<210> SEQ ID NO 64
<211> LENGTH: 18
<212> TYPE: PRT
<213> ORGANISM: Artificial Sequence
<220> FEATURE:
<223> OTHER INFORMATION: Synthetic peptide

<400> SEQUENCE: 64

Arg Arg Arg Arg Arg Arg Arg Arg Arg Leu Pro Asp Cys Tyr Asp Thr
1               5                   10                  15

Pro Leu

<210> SEQ ID NO 65
<211> LENGTH: 18
<212> TYPE: PRT
<213> ORGANISM: Artificial Sequence
<220> FEATURE:
<223> OTHER INFORMATION: Synthetic peptide

<400> SEQUENCE: 65

Lys Lys Lys Lys Lys Lys Lys Lys Lys Leu Pro Asp Cys Tyr Asp Thr

Pro Leu

<210> SEQ ID NO 66
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 66

Tyr Gly Arg Lys Lys Arg Arg Gln Arg Arg Arg Leu Pro Asp Cys Tyr
1               5                   10                  15

Asp Thr Pro Leu
            20

<210> SEQ ID NO 67
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 67

Arg Arg Arg Arg Arg Arg Arg Arg Arg Leu Pro Asp Cys Tyr Asp Thr
1               5                   10                  15

Pro Leu

<210> SEQ ID NO 68
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 68

Lys Lys Lys Lys Lys Lys Lys Lys Lys Leu Pro Asp Cys Tyr Asp Thr
1               5                   10                  15

Pro Leu

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 69

Leu Pro Asp Cys Tyr Asp Thr Pro Leu
1               5

```
<210> SEQ ID NO 70
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 70

Leu Pro Asp Cys Tyr Asp Thr Pro Leu
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

<400> SEQUENCE: 71

Leu Pro Asp Cys Tyr Asp Thr Pro Leu
1               5

<210> SEQ ID NO 72
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 72

Gly Leu Pro Asp Cys Tyr Asp Thr Pro Leu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 73

Gly Leu Pro Asp Cys Tyr Asp Thr Pro Leu
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 74

Gly Leu Pro Asp Cys Tyr Asp Thr Pro Leu
1               5                   10

<210> SEQ ID NO 75
<211> LENGTH: 20
<212> TYPE: PRT
<213> ORGANISM: Artificial Sequence
<220> FEATURE:
<223> OTHER INFORMATION: Synthetic peptide

<400> SEQUENCE: 75

Tyr Gly Arg Lys Lys Arg Arg Gln Arg Arg Leu Pro Asn Cys Tyr
1               5                   10                  15

Asn Thr Pro Leu
            20

<210> SEQ ID NO 76
<211> LENGTH: 18
<212> TYPE: PRT
<213> ORGANISM: Artificial Sequence
<220> FEATURE:
<223> OTHER INFORMATION: Synthetic peptide

<400> SEQUENCE: 76

Arg Arg Arg Arg Arg Arg Arg Arg Arg Leu Pro Asn Cys Tyr Asn Thr
1               5                   10                  15

Pro Leu

<210> SEQ ID NO 77
<211> LENGTH: 18
<212> TYPE: PRT
<213> ORGANISM: Artificial Sequence
<220> FEATURE:
<223> OTHER INFORMATION: Synthetic peptide

<400> SEQUENCE: 77

Lys Lys Lys Lys Lys Lys Lys Lys Lys Leu Pro Asn Cys Tyr Asn Thr
1               5                   10                  15

Pro Leu

<210> SEQ ID NO 78
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 78

Tyr Gly Arg Lys Lys Arg Arg Gln Arg Arg Leu Pro Asn Cys Tyr
1               5                   10                  15

Asn Thr Pro Leu
            20
```

```
<210> SEQ ID NO 79
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 79

Arg Arg Arg Arg Arg Arg Arg Arg Arg Leu Pro Asn Cys Tyr Asn Thr
 1               5                  10                  15

Pro Leu

<210> SEQ ID NO 80
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 80

Lys Lys Lys Lys Lys Lys Lys Lys Lys Leu Pro Asn Cys Tyr Asn Thr
 1               5                  10                  15

Pro Leu

<210> SEQ ID NO 81
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 81

Leu Pro Asn Cys Tyr Asn Thr Pro Leu
 1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

<400> SEQUENCE: 82

Leu Pro Asn Cys Tyr Asn Thr Pro Leu
 1               5

<210> SEQ ID NO 83
```

```
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 83

Leu Pro Asn Cys Tyr Asn Thr Pro Leu
1               5

<210> SEQ ID NO 84
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 84

Gly Leu Pro Asn Cys Tyr Asn Thr Pro Leu
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 85

Gly Leu Pro Asn Cys Tyr Asn Thr Pro Leu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 86

Gly Leu Pro Asn Cys Tyr Asn Thr Pro Leu
1               5                   10

<210> SEQ ID NO 87
<211> LENGTH: 20
<212> TYPE: PRT
<213> ORGANISM: Artificial Sequence
<220> FEATURE:
<223> OTHER INFORMATION: Synthetic peptide

<400> SEQUENCE: 87
```

Tyr Gly Arg Lys Lys Arg Arg Gln Arg Arg Leu Pro Asp Tyr Tyr
1               5                   10                  15

Asp Thr Pro Leu
            20

<210> SEQ ID NO 88
<211> LENGTH: 18
<212> TYPE: PRT
<213> ORGANISM: Artificial Sequence
<220> FEATURE:
<223> OTHER INFORMATION: Synthetic peptide

<400> SEQUENCE: 88

Arg Arg Arg Arg Arg Arg Arg Arg Arg Leu Pro Asp Tyr Tyr Asp Thr
1               5                   10                  15

Pro Leu

<210> SEQ ID NO 89
<211> LENGTH: 18
<212> TYPE: PRT
<213> ORGANISM: Artificial Sequence
<220> FEATURE:
<223> OTHER INFORMATION: Synthetic peptide

<400> SEQUENCE: 89

Lys Lys Lys Lys Lys Lys Lys Lys Lys Leu Pro Asp Tyr Tyr Asp Thr
1               5                   10                  15

Pro Leu

<210> SEQ ID NO 90
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 90

Tyr Gly Arg Lys Lys Arg Arg Gln Arg Arg Leu Pro Asp Tyr Tyr
1               5                   10                  15

Asp Thr Pro Leu
            20

<210> SEQ ID NO 91
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 91

Arg Arg Arg Arg Arg Arg Arg Arg Arg Leu Pro Asp Tyr Tyr Asp Thr
1               5                   10                  15

Pro Leu

<210> SEQ ID NO 92
<211> LENGTH: 18

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 92

Lys Lys Lys Lys Lys Lys Lys Lys Lys Leu Pro Asp Tyr Tyr Asp Thr
1               5                   10                  15

Pro Leu

<210> SEQ ID NO 93
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 93

Leu Pro Asp Tyr Tyr Asp Thr Pro Leu
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

<400> SEQUENCE: 94

Leu Pro Asp Tyr Tyr Asp Thr Pro Leu
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 95

Leu Pro Asp Tyr Tyr Asp Thr Pro Leu
1               5

<210> SEQ ID NO 96
<211> LENGTH: 10
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MOD_RES
<222> LOCATION: (10)..(10)
<223> OTHER INFORMATION: AMIDATION

<400> SEQUENCE: 96

Gly Leu Pro Asp Tyr Tyr Asp Thr Pro Leu
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 97

Gly Leu Pro Asp Tyr Tyr Asp Thr Pro Leu
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 98

Gly Leu Pro Asp Tyr Tyr Asp Thr Pro Leu
1               5                   10

<210> SEQ ID NO 99
<211> LENGTH: 20
<212> TYPE: PRT
<213> ORGANISM: Artificial Sequence
<220> FEATURE:
<223> OTHER INFORMATION: Synthetic peptide

<400> SEQUENCE: 99

Tyr Gly Arg Lys Lys Arg Arg Gln Arg Arg Leu Pro Asn Tyr Tyr
1               5                   10                  15

Asn Thr Pro Leu
            20

<210> SEQ ID NO 100
<211> LENGTH: 18
<212> TYPE: PRT
<213> ORGANISM: Artificial Sequence
<220> FEATURE:
<223> OTHER INFORMATION: Synthetic peptide

<400> SEQUENCE: 100

Arg Arg Arg Arg Arg Arg Arg Arg Arg Leu Pro Asn Tyr Tyr Asn Thr
1               5                   10                  15

Pro Leu
```

```
<210> SEQ ID NO 101
<211> LENGTH: 18
<212> TYPE: PRT
<213> ORGANISM: Artificial Sequence
<220> FEATURE:
<223> OTHER INFORMATION: Synthetic peptide

<400> SEQUENCE: 101

Lys Lys Lys Lys Lys Lys Lys Lys Lys Leu Pro Asn Tyr Tyr Asn Thr
1               5                   10                  15

Pro Leu

<210> SEQ ID NO 102
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 102

Tyr Gly Arg Lys Lys Arg Arg Gln Arg Arg Leu Pro Asn Tyr Tyr
1               5                   10                  15

Asn Thr Pro Leu
            20

<210> SEQ ID NO 103
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 103

Arg Arg Arg Arg Arg Arg Arg Arg Arg Leu Pro Asn Tyr Tyr Asn Thr
1               5                   10                  15

Pro Leu

<210> SEQ ID NO 104
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 104

Lys Lys Lys Lys Lys Lys Lys Lys Lys Leu Pro Asn Tyr Tyr Asn Thr
1               5                   10                  15

Pro Leu

<210> SEQ ID NO 105
<211> LENGTH: 9
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (9)..(9)
<223> OTHER INFORMATION: AMIDATION

<400> SEQUENCE: 105

Leu Pro Asn Tyr Tyr Asn Thr Pro Leu
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

<400> SEQUENCE: 106

Leu Pro Asn Tyr Tyr Asn Thr Pro Leu
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 107

Leu Pro Asn Tyr Tyr Asn Thr Pro Leu
1               5

<210> SEQ ID NO 108
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 108

Gly Leu Pro Asn Tyr Tyr Asn Thr Pro Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
```

<223> OTHER INFORMATION: AMIDATION

<400> SEQUENCE: 109

Gly Leu Pro Asn Tyr Tyr Asn Thr Pro Leu
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 110

Gly Leu Pro Asn Tyr Tyr Asn Thr Pro Leu
1               5                   10

<210> SEQ ID NO 111
<211> LENGTH: 20
<212> TYPE: PRT
<213> ORGANISM: Artificial Sequence
<220> FEATURE:
<223> OTHER INFORMATION: Synthetic peptide

<400> SEQUENCE: 111

Tyr Gly Arg Lys Lys Arg Arg Gln Arg Arg Asp Gln His Ser Gln
1               5                   10                  15

Ile Thr Lys Val
            20

<210> SEQ ID NO 112
<211> LENGTH: 18
<212> TYPE: PRT
<213> ORGANISM: Artificial Sequence
<220> FEATURE:
<223> OTHER INFORMATION: Synthetic peptide

<400> SEQUENCE: 112

Arg Arg Arg Arg Arg Arg Arg Arg Arg Asp Gln His Ser Gln Ile Thr
1               5                   10                  15

Lys Val

<210> SEQ ID NO 113
<211> LENGTH: 18
<212> TYPE: PRT
<213> ORGANISM: Artificial Sequence
<220> FEATURE:
<223> OTHER INFORMATION: Synthetic peptide

<400> SEQUENCE: 113

Lys Lys Lys Lys Lys Lys Lys Lys Lys Asp Gln His Ser Gln Ile Thr
1               5                   10                  15

Lys Val

<210> SEQ ID NO 114
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES

```
<222> LOCATION: (20)..(20)
<223> OTHER INFORMATION: AMIDATION

<400> SEQUENCE: 114

Tyr Gly Arg Lys Lys Arg Arg Gln Arg Arg Asp Gln His Ser Gln
1               5                   10                  15

Ile Thr Lys Val
            20

<210> SEQ ID NO 115
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 115

Arg Arg Arg Arg Arg Arg Arg Arg Arg Asp Gln His Ser Gln Ile Thr
1               5                   10                  15

Lys Val

<210> SEQ ID NO 116
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 116

Lys Lys Lys Lys Lys Lys Lys Lys Lys Asp Gln His Ser Gln Ile Thr
1               5                   10                  15

Lys Val

<210> SEQ ID NO 117
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 117

Asp Gln His Ser Gln Ile Thr Lys Val
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
```

```
<222> LOCATION: (9)..(9)
<223> OTHER INFORMATION: AMIDATION

<400> SEQUENCE: 118

Asp Gln His Ser Gln Ile Thr Lys Val
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 119

Asp Gln His Ser Gln Ile Thr Lys Val
1               5

<210> SEQ ID NO 120
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 120

Gly Asp Gln His Ser Gln Ile Thr Lys Val
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 121

Gly Asp Gln His Ser Gln Ile Thr Lys Val
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 122

Gly Asp Gln His Ser Gln Ile Thr Lys Val
1               5                   10
```

<210> SEQ ID NO 123
<211> LENGTH: 20
<212> TYPE: PRT
<213> ORGANISM: Artificial Sequence
<220> FEATURE:
<223> OTHER INFORMATION: Synthetic peptide

<400> SEQUENCE: 123

Tyr Gly Arg Lys Lys Arg Arg Gln Arg Arg Asn Gln His Ser Gln
1               5                   10                  15

Ile Thr Lys Val
            20

<210> SEQ ID NO 124
<211> LENGTH: 18
<212> TYPE: PRT
<213> ORGANISM: Artificial Sequence
<220> FEATURE:
<223> OTHER INFORMATION: Synthetic peptide

<400> SEQUENCE: 124

Arg Arg Arg Arg Arg Arg Arg Arg Arg Asn Gln His Ser Gln Ile Thr
1               5                   10                  15

Lys Val

<210> SEQ ID NO 125
<211> LENGTH: 18
<212> TYPE: PRT
<213> ORGANISM: Artificial Sequence
<220> FEATURE:
<223> OTHER INFORMATION: Synthetic peptide

<400> SEQUENCE: 125

Lys Lys Lys Lys Lys Lys Lys Lys Lys Asn Gln His Ser Gln Ile Thr
1               5                   10                  15

Lys Val

<210> SEQ ID NO 126
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 126

Tyr Gly Arg Lys Lys Arg Arg Gln Arg Arg Asn Gln His Ser Gln
1               5                   10                  15

Ile Thr Lys Val
            20

<210> SEQ ID NO 127
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

```
<400> SEQUENCE: 127

Arg Arg Arg Arg Arg Arg Arg Arg Arg Asn Gln His Ser Gln Ile Thr
1               5                   10                  15

Lys Val

<210> SEQ ID NO 128
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 128

Lys Lys Lys Lys Lys Lys Lys Lys Lys Asn Gln His Ser Gln Ile Thr
1               5                   10                  15

Lys Val

<210> SEQ ID NO 129
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 129

Asn Gln His Ser Gln Ile Thr Lys Val
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

<400> SEQUENCE: 130

Asn Gln His Ser Gln Ile Thr Lys Val
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 131

Asn Gln His Ser Gln Ile Thr Lys Val
```

```
1               5
```

<210> SEQ ID NO 132
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 132

```
Gly Asn Gln His Ser Gln Ile Thr Lys Val
1               5                   10
```

<210> SEQ ID NO 133
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 133

```
Gly Asn Gln His Ser Gln Ile Thr Lys Val
1               5                   10
```

<210> SEQ ID NO 134
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 134

```
Gly Asn Gln His Ser Gln Ile Thr Lys Val
1               5                   10
```

<210> SEQ ID NO 135
<211> LENGTH: 20
<212> TYPE: PRT
<213> ORGANISM: Artificial Sequence
<220> FEATURE:
<223> OTHER INFORMATION: Synthetic peptide

<400> SEQUENCE: 135

```
Tyr Gly Arg Lys Lys Arg Arg Gln Arg Arg Arg Asp Gln His Thr Gln
1               5                   10                  15

Ile Thr Lys Val
            20
```

<210> SEQ ID NO 136
<211> LENGTH: 18
<212> TYPE: PRT
<213> ORGANISM: Artificial Sequence
<220> FEATURE:

<223> OTHER INFORMATION: Synthetic peptide

<400> SEQUENCE: 136

Arg Arg Arg Arg Arg Arg Arg Arg Arg Asp Gln His Thr Gln Ile Thr
1               5                   10                  15

Lys Val

<210> SEQ ID NO 137
<211> LENGTH: 18
<212> TYPE: PRT
<213> ORGANISM: Artificial Sequence
<220> FEATURE:
<223> OTHER INFORMATION: Synthetic peptide

<400> SEQUENCE: 137

Lys Lys Lys Lys Lys Lys Lys Lys Lys Asp Gln His Thr Gln Ile Thr
1               5                   10                  15

Lys Val

<210> SEQ ID NO 138
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 138

Tyr Gly Arg Lys Lys Arg Arg Gln Arg Arg Arg Asp Gln His Thr Gln
1               5                   10                  15

Ile Thr Lys Val
            20

<210> SEQ ID NO 139
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 139

Arg Arg Arg Arg Arg Arg Arg Arg Arg Asp Gln His Thr Gln Ile Thr
1               5                   10                  15

Lys Val

<210> SEQ ID NO 140
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 140

Lys Lys Lys Lys Lys Lys Lys Lys Lys Asp Gln His Thr Gln Ile Thr
1               5                   10                  15

```
<210> SEQ ID NO 141
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 141

Asp Gln His Thr Gln Ile Thr Lys Val
1               5

<210> SEQ ID NO 142
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 142

Asp Gln His Thr Gln Ile Thr Lys Val Val
1               5                   10

<210> SEQ ID NO 143
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 143

Asp Gln His Thr Gln Ile Thr Lys Val
1               5

<210> SEQ ID NO 144
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 144

Gly Asp Gln His Thr Gln Ile Thr Lys Val
1               5                   10

<210> SEQ ID NO 145
<211> LENGTH: 10
<212> TYPE: PRT
```

(Lys Val continued from previous page before SEQ ID NO 141)

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 145

Gly Asp Gln His Thr Gln Ile Thr Lys Val
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 146

Gly Asp Gln His Thr Gln Ile Thr Lys Val
1               5                   10

<210> SEQ ID NO 147
<211> LENGTH: 20
<212> TYPE: PRT
<213> ORGANISM: Artificial Sequence
<220> FEATURE:
<223> OTHER INFORMATION: Synthetic peptide

<400> SEQUENCE: 147

Tyr Gly Arg Lys Lys Arg Arg Gln Arg Arg Asn Gln His Thr Gln
1               5                   10                  15

Ile Thr Lys Val
            20

<210> SEQ ID NO 148
<211> LENGTH: 18
<212> TYPE: PRT
<213> ORGANISM: Artificial Sequence
<220> FEATURE:
<223> OTHER INFORMATION: Synthetic peptide

<400> SEQUENCE: 148

Arg Arg Arg Arg Arg Arg Arg Arg Arg Asn Gln His Thr Gln Ile Thr
1               5                   10                  15

Lys Val

<210> SEQ ID NO 149
<211> LENGTH: 18
<212> TYPE: PRT
<213> ORGANISM: Artificial Sequence
<220> FEATURE:
<223> OTHER INFORMATION: Synthetic peptide

<400> SEQUENCE: 149

Lys Lys Lys Lys Lys Lys Lys Lys Asn Gln His Thr Gln Ile Thr
1               5                   10                  15

Lys Val
```

```
<210> SEQ ID NO 150
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 150

Tyr Gly Arg Lys Lys Arg Arg Gln Arg Arg Asn Gln His Thr Gln
1               5                   10                  15

Ile Thr Lys Val
            20

<210> SEQ ID NO 151
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 151

Arg Arg Arg Arg Arg Arg Arg Arg Arg Asn Gln His Thr Gln Ile Thr
1               5                   10                  15

Lys Val

<210> SEQ ID NO 152
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 152

Lys Lys Lys Lys Lys Lys Lys Lys Lys Asn Gln His Thr Gln Ile Thr
1               5                   10                  15

Lys Val

<210> SEQ ID NO 153
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 153

Asn Gln His Thr Gln Ile Thr Lys Val
1               5

<210> SEQ ID NO 154
<211> LENGTH: 9
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

<400> SEQUENCE: 154

Asn Gln His Thr Gln Ile Thr Lys Val
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 155

Asn Gln His Thr Gln Ile Thr Lys Val
1               5

<210> SEQ ID NO 156
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 156

Gly Asn Gln His Thr Gln Ile Thr Lys Val
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 157

Gly Asn Gln His Thr Gln Ile Thr Lys Val
1               5                   10

<210> SEQ ID NO 158
<211> LENGTH: 10
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 158

Gly Asn Gln His Ser Gln Ile Thr Lys Val
1               5                   10

<210> SEQ ID NO 159
<211> LENGTH: 20
<212> TYPE: PRT
<213> ORGANISM: Artificial Sequence
<220> FEATURE:
<223> OTHER INFORMATION: Synthetic peptide

<400> SEQUENCE: 159

Tyr Gly Arg Lys Lys Arg Arg Gln Arg Arg Arg Phe His Asp Phe Asp
1               5                   10                  15

Tyr Val Ala Asp
            20

<210> SEQ ID NO 160
<211> LENGTH: 18
<212> TYPE: PRT
<213> ORGANISM: Artificial Sequence
<220> FEATURE:
<223> OTHER INFORMATION: Synthetic peptide

<400> SEQUENCE: 160

Arg Arg Arg Arg Arg Arg Arg Arg Arg Phe His Asp Phe Asp Tyr Val
1               5                   10                  15

Ala Asp

<210> SEQ ID NO 161
<211> LENGTH: 18
<212> TYPE: PRT
<213> ORGANISM: Artificial Sequence
<220> FEATURE:
<223> OTHER INFORMATION: Synthetic peptide

<400> SEQUENCE: 161

Lys Lys Lys Lys Lys Lys Lys Lys Lys Phe His Asp Phe Asp Tyr Val
1               5                   10                  15

Ala Asp

<210> SEQ ID NO 162
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 162

Tyr Gly Arg Lys Lys Arg Arg Gln Arg Arg Phe His Asp Phe Asp
1               5                   10                  15

Tyr Val Ala Asp
            20

<210> SEQ ID NO 163
```

```
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 163

Arg Arg Arg Arg Arg Arg Arg Arg Arg Phe His Asp Phe Asp Tyr Val
1               5                   10                  15

Ala Asp

<210> SEQ ID NO 164
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 164

Lys Lys Lys Lys Lys Lys Lys Lys Lys Phe His Asp Phe Asp Tyr Val
1               5                   10                  15

Ala Asp

<210> SEQ ID NO 165
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 165

Phe His Asp Phe Asp Tyr Val Ala Asp
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

<400> SEQUENCE: 166

Phe His Asp Phe Asp Tyr Val Ala Asp
1               5

<210> SEQ ID NO 167
<211> LENGTH: 9
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 167

Phe His Asp Phe Asp Tyr Val Ala Asp
1               5

<210> SEQ ID NO 168
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 168

Gly Phe His Asp Phe Asp Tyr Val Ala Asp
1               5                  10

<210> SEQ ID NO 169
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 169

Gly Phe His Asp Phe Asp Tyr Val Ala Asp
1               5                  10

<210> SEQ ID NO 170
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 170

Gly Phe His Asp Phe Asp Tyr Val Ala Asp
1               5                  10

<210> SEQ ID NO 171
<211> LENGTH: 20
<212> TYPE: PRT
<213> ORGANISM: Artificial Sequence
<220> FEATURE:
<223> OTHER INFORMATION: Synthetic peptide

<400> SEQUENCE: 171

Tyr Gly Arg Lys Lys Arg Arg Gln Arg Arg Phe His Asn Phe Asn
1               5                  10                  15
```

Tyr Val Ala Asn
        20

<210> SEQ ID NO 172
<211> LENGTH: 18
<212> TYPE: PRT
<213> ORGANISM: Artificial Sequence
<220> FEATURE:
<223> OTHER INFORMATION: Synthetic peptide

<400> SEQUENCE: 172

Arg Arg Arg Arg Arg Arg Arg Arg Arg Phe His Asn Phe Asn Tyr Val
1               5                   10                  15

Ala Asn

<210> SEQ ID NO 173
<211> LENGTH: 18
<212> TYPE: PRT
<213> ORGANISM: Artificial Sequence
<220> FEATURE:
<223> OTHER INFORMATION: Synthetic peptide

<400> SEQUENCE: 173

Lys Lys Lys Lys Lys Lys Lys Lys Lys Phe His Asn Phe Asn Tyr Val
1               5                   10                  15

Ala Asn

<210> SEQ ID NO 174
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 174

Tyr Gly Arg Lys Lys Arg Arg Gln Arg Arg Arg Phe His Asn Phe Asn
1               5                   10                  15

Tyr Val Ala Asn
        20

<210> SEQ ID NO 175
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 175

Arg Arg Arg Arg Arg Arg Arg Arg Arg Phe His Asn Phe Asn Tyr Val
1               5                   10                  15

Ala Asn

<210> SEQ ID NO 176
<211> LENGTH: 18
<212> TYPE: PRT
<213> ORGANISM: Artificial Sequence
<220> FEATURE:

```
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 176

Lys Lys Lys Lys Lys Lys Lys Lys Lys Phe His Asn Phe Asn Tyr Val
1               5                   10                  15
Ala Asn

<210> SEQ ID NO 177
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 177

Phe His Asn Phe Asn Tyr Val Ala Asn
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

<400> SEQUENCE: 178

Phe His Asn Phe Asn Tyr Val Ala Asn
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 179

Phe His Asn Phe Asn Tyr Val Ala Asn
1               5

<210> SEQ ID NO 180
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION
```

```
<400> SEQUENCE: 180

Gly Phe His Asn Phe Asn Tyr Val Ala Asn
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 181

Gly Phe His Asn Phe Asn Tyr Val Ala Asn
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 182

Gly Phe His Asn Phe Asn Tyr Val Ala Asn
1               5                   10

<210> SEQ ID NO 183
<211> LENGTH: 20
<212> TYPE: PRT
<213> ORGANISM: Artificial Sequence
<220> FEATURE:
<223> OTHER INFORMATION: Synthetic peptide

<400> SEQUENCE: 183

Tyr Gly Arg Lys Lys Arg Arg Gln Arg Arg Arg Phe Arg Asp Phe Asp
1               5                   10                  15

Tyr Ile Ala Asp
            20

<210> SEQ ID NO 184
<211> LENGTH: 18
<212> TYPE: PRT
<213> ORGANISM: Artificial Sequence
<220> FEATURE:
<223> OTHER INFORMATION: Synthetic peptide

<400> SEQUENCE: 184

Arg Arg Arg Arg Arg Arg Arg Arg Arg Phe Arg Asp Phe Asp Tyr Ile
1               5                   10                  15

Ala Asp

<210> SEQ ID NO 185
<211> LENGTH: 18
<212> TYPE: PRT
```

```
<213> ORGANISM: Artificial Sequence
<220> FEATURE:
<223> OTHER INFORMATION: Synthetic peptide

<400> SEQUENCE: 185

Lys Lys Lys Lys Lys Lys Lys Lys Lys Phe Arg Asp Phe Asp Tyr Ile
1               5                   10                  15

Ala Asp

<210> SEQ ID NO 186
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 186

Tyr Gly Arg Lys Lys Arg Arg Gln Arg Arg Arg Phe Arg Asp Phe Asp
1               5                   10                  15

Tyr Ile Ala Asp
            20

<210> SEQ ID NO 187
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 187

Arg Arg Arg Arg Arg Arg Arg Arg Arg Phe Arg Asp Phe Asp Tyr Ile
1               5                   10                  15

Ala Asp

<210> SEQ ID NO 188
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 188

Lys Lys Lys Lys Lys Lys Lys Lys Lys Phe Arg Asp Phe Asp Tyr Ile
1               5                   10                  15

Ala Asp

<210> SEQ ID NO 189
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
```

```
<223> OTHER INFORMATION: AMIDATION

<400> SEQUENCE: 189

Phe Arg Asp Phe Asp Tyr Ile Ala Asp
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

<400> SEQUENCE: 190

Phe Arg Asp Phe Asp Tyr Ile Ala Asp
1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 191

Phe Arg Asp Phe Asp Tyr Ile Ala Asp
1               5

<210> SEQ ID NO 192
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 192

Gly Phe Arg Asp Phe Asp Tyr Ile Ala Asp
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 193
```

```
Gly Phe Arg Asp Phe Asp Tyr Ile Ala Asp
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 194

Gly Phe Arg Asp Phe Asp Tyr Ile Ala Asp
1               5                   10

<210> SEQ ID NO 195
<211> LENGTH: 20
<212> TYPE: PRT
<213> ORGANISM: Artificial Sequence
<220> FEATURE:
<223> OTHER INFORMATION: Synthetic peptide

<400> SEQUENCE: 195

Tyr Gly Arg Lys Lys Arg Arg Gln Arg Arg Phe Arg Asn Phe Asn
1               5                   10                  15

Tyr Ile Ala Asn
            20

<210> SEQ ID NO 196
<211> LENGTH: 18
<212> TYPE: PRT
<213> ORGANISM: Artificial Sequence
<220> FEATURE:
<223> OTHER INFORMATION: Synthetic peptide

<400> SEQUENCE: 196

Arg Arg Arg Arg Arg Arg Arg Arg Arg Phe Arg Asn Phe Asn Tyr Ile
1               5                   10                  15

Ala Asn

<210> SEQ ID NO 197
<211> LENGTH: 18
<212> TYPE: PRT
<213> ORGANISM: Artificial Sequence
<220> FEATURE:
<223> OTHER INFORMATION: Synthetic peptide

<400> SEQUENCE: 197

Lys Lys Lys Lys Lys Lys Lys Lys Lys Phe Arg Asn Phe Asn Tyr Ile
1               5                   10                  15

Ala Asn

<210> SEQ ID NO 198
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION
```

<400> SEQUENCE: 198

Tyr Gly Arg Lys Lys Arg Arg Gln Arg Arg Phe Arg Asn Phe Asn
1               5                   10                  15

Tyr Ile Ala Asn
            20

<210> SEQ ID NO 199
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 199

Arg Arg Arg Arg Arg Arg Arg Arg Arg Phe Arg Asn Phe Asn Tyr Ile
1               5                   10                  15

Ala Asn

<210> SEQ ID NO 200
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: AMIDATION

<400> SEQUENCE: 200

Lys Lys Lys Lys Lys Lys Lys Lys Lys Phe Arg Asn Phe Asn Tyr Ile
1               5                   10                  15

Ala Asn

<210> SEQ ID NO 201
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 201

Phe Arg Asn Phe Asn Tyr Ile Ala Asn
1               5

<210> SEQ ID NO 202
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (9)..(9)
<223> OTHER INFORMATION: AMIDATION

```
<400> SEQUENCE: 202

Phe Arg Asn Phe Asn Tyr Ile Ala Asn
1               5

<210> SEQ ID NO 203
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 203

Phe Arg Asn Phe Asn Tyr Ile Ala Asn
1               5

<210> SEQ ID NO 204
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 204

Gly Phe Arg Asn Phe Asn Tyr Ile Ala Asn
1               5                   10

<210> SEQ ID NO 205
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation
<220> FEATURE:
<221> NAME/KEY: MOD_RES
<222> LOCATION: (10)..(10)
<223> OTHER INFORMATION: AMIDATION

<400> SEQUENCE: 205

Gly Phe Arg Asn Phe Asn Tyr Ile Ala Asn
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristoylation

<400> SEQUENCE: 206

Gly Phe Arg Asn Phe Asn Tyr Ile Ala Asn
1               5                   10

<210> SEQ ID NO 207
```

```
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa denotes any amino acid residue.

<400> SEQUENCE: 207

Phe Xaa Xaa Phe Asp Tyr
1               5

<210> SEQ ID NO 208
<211> LENGTH: 24
<212> TYPE: PRT
<213> ORGANISM: Artificial Sequence
<220> FEATURE:
<223> OTHER INFORMATION: Synthetic peptide

<400> SEQUENCE: 208

Arg Glu Pro Arg Ile Leu Ser Glu Glu Gln Glu Met Phe Arg Asp
1               5                   10                  15

Phe Asp Tyr Ile Ala Asp Trp Cys
            20
```

PEPTIDES AND METHOD FOR TREATMENT OF CARDIAC ARREST

INTRODUCTION

This application is a U.S. National Stage Application of PCT/US2016/060789 filed Nov. 7, 2016 and claims benefit of priority to U.S. Provisional Patent Application Ser. No. 62/252,201, filed Nov. 6, 2015, the contents of each of which is are incorporated herein by reference in its their entirety.

BACKGROUND

Cardiac Arrest, or Sudden Death, is a descriptor for a diverse collection of physiological abnormalities with a common cardiac etiology, wherein the patient typically presents with the symptoms of pulselessness, apnoea, and unconsciousness. Cardiac arrest is widespread, with an estimated 300,000 victims annually in the U.S. alone and a similar estimate of additional victims worldwide. Sudden cardiac arrest is a leading cause of death in the United States, with a greater public health impact in measures of mortality than cancer, HIV, stroke or infectious diseases. Approximately 40-50% of cardiac arrest victims are resuscitated by paramedics and emergency medical technicians (EMTs) in the field and brought to the hospital for further treatment; however, due to the insult on the victim's vital organs from the cardiac arrest, typically only about 25% (or approximately 40,000 out of 600,000 cardiac arrest victims, worldwide) of those victims who survive to the hospital will survive to being discharged from the hospital.

The treatment window for cardiac arrest with current treatments of defibrillation, cardiopulmonary resuscitation, and inotropic (e.g., epinephrine) drug treatment is very narrow. Long term survival rates from the time of victim collapse decrease at a roughly exponential rate with a time constant of roughly 2 minutes. Thus, just two minutes of delay in treatment using the currently recommended treatment protocols result in a long term survival rate of 30-35%. After 15 minutes, the long term survival rates are below 5%.

During cardiac arrest, cerebral blood flow ceases and global cerebral hypoxic-ischemic injury begins within minutes. Myocardial and neuronal tissue is able to remain viable during prolonged periods of ischemia (as long as twenty minutes), but paradoxically will sustain immediate damage during the return of circulation and oxygenation. It has been shown in a variety of studies at the tissue-level and animal model that successful resuscitation with return of spontaneous circulation (ROSC) leads to a secondary cascade of injury related to reperfusion injury. This reperfusion injury is particularly acute in neuronal tissue.

After successful cardiac resuscitation and ROSC, cerebral blood flow may remain abnormally low for several hours. After an initial hyperemia resulting from high circulating levels of catecholamines, cerebral blood flow decreases just as the cerebral metabolic rate for oxygen increases. This can lead to a prolonged state of relative cerebral ischemia. This prolonged mismatch between cerebral metabolic rate and blood flow, and ongoing biochemical and molecular processes related to delayed neuronal apoptotic and necrotic cell death, provide the scientific rationale for induced hypothermia as a form of neuroprotection after cardiac arrest. One method developed is the cooling of comatose cardiac arrest survivors to approximately 34° C. within 4 hours of arrest onset, which has been shown in several studies to enhance the survival rates of patients who are initially resuscitated (the approximately 40-50% of victims making it to the hospital). Hypothermia is common in the cardiac intensive care, hospital environment such as in bypass operations, etc, but there are two related drawbacks of hypothermia which have prevented its widespread use in the pre-hospital environment.

The first of these drawbacks is the primary biomedical engineering challenge of hypothermia: the large thermal mass of the victim and the difficulty of cooling the victim quickly and safely. While it has been shown that hypothermia is beneficial as long as it is applied within 4 hours of cardiac arrest, studies have also shown that cooling prior to resuscitation provides additive therapeutic benefits. While the causes for this are only speculative, one of the factors is likely the positive effects of hypothermia during the reperfusion phase of resuscitation. Practically speaking, it is highly undesirable to delay defibrillation and resuscitation to cool a patient to the proper temperature. Non-invasive methods of cooling take at minimum 10 minutes to 1 hour, while invasive methods such as extraction and cooling of the blood may take only 3-5 minutes, but are hazardous to the patient, particularly in the pre-hospital environment. In the case of defibrillation, even a delay of 3 minutes can result in a decrease in survival of 30%. While hypothermia may be effective at counteracting longer-term deleterious effects of ischemia and reperfusion, it would be desirable to have a treatment that can provide immediate protective effects against reperfusion injury while, at the same time, not delaying any current resuscitation interventions.

The phosphatidylinositol-3 kinase (PI3K)/protein kinase B (PKB or Akt) pathway is pivotal for cellular homeostasis, neurological development, metabolism, and other processes. It regulates various aspects of cellular development such as apoptosis, cell cycle progression, and cell differentiation. The lipid phosphatase and tensin homolog (PTEN), which dephosphorylates $PIP_3$ to $PIP_2$, has been shown to limit Akt activation by decreasing $PIP_3$. Deletion or mutation of PTEN is observed in many types of tumors and is accompanied by high Akt activity. Further, protein kinase N2 (PKN2), also known as protein kinase C-related kinase-2 (PRK2), may negatively regulate Akt by inhibiting phosphoinositide-dependent kinase 1 (PDK1) activation of Akt. The kinase domain of PDK1 interacts with a region of PRK2 encompassing the PDK1-interacting fragment (PIF) including the hydrophobic motif FXXFDY (SEQ ID NO:207) (Balendran, et al. (1999) *Curr. Biol.* 9:393-404). Moreover, protein phosphatase (PP)2A is known to dephosphorylate Akt at Thr308 and/or Ser473 in noncardiac cells. A pharmacological study also suggests that in retina PP2B (calcineurin) can dephosphorylate Akt at both sites. A more specific Akt-directed PP2C family member protein phosphatase, PHLPP (pleckstrin homology (PH) domain leucine-rich repeat protein phosphatase), has been identified. Two isoforms of PHLPP, PHLPP-1 and PHLPP-2, have been shown to selectively dephosphorylate the hydrophobic motif of Akt (Ser473) via the PDZ binding motif (Gao, et al. (2005) *Mol. Cell* 18:13-24) thereby terminating Akt signaling. PHLPP levels are markedly reduced in several cancer cell lines, resulting in elevated Akt activation. Conversely heterologous expression of PHLPP in cancer cells can prevent Akt activation and promote apoptotic death. In this respect, the administration of PHLPP has been suggested for use in the treatment of cancer (US 2008/0108569).

In cardiac myocytes, overexpression of PTEN has been shown to be proapoptotic, whereas genetic deletion of PTEN rescues hearts from ischemia/reperfusion (I/R) injury (Schwartzbauer & Robbins (2001) *J. Biol. Chem.* 276: 35786-93; Ruan, et al. (2009) *J. Mol. Cell Cardiol.* 46:193-

200). Similarly, PHLPP-1 knockdown via siRNA or knockout in cardiomyocytes potentiates Akt phosphorylation at 5473 induced by agonists (Miyamoto, et al. (2010) *Circ. Res.* 107:476-84).

In support of a role for PTEN in I/R injury and protection, it has been demonstrated that VO-OHpic (VO), a vanadyl small molecule compound that demonstrates potent inhibition of PTEN, induces cooling-like cardioprotection with an almost four-fold reduction in cell death and significant increase of phosphorylated Akt (Zhu, et al. (2014) *PLoS One* 9:e95622), as well as improved recovery and survival in an established mouse model of SCA (Li, et al. (2015) *Am. J. Physiol. Heart Circ. Physiol.* 308:H1414-22). Similarly, the use of insulin has been suggested to decrease PHLPP-1 protein levels, activate Akt phosphorylation, promote myocardial cell survival, and afford protection of the ischemic heart (CN 201210382244).

Peptides DQHSQITKV (SEQ ID NO:4) and DQHTQ-ITKV (SEQ ID NO:5), based on the PDZ domains of rat and human PTEN proteins, respectively, have been described for use in treating a retinal degenerative disorder or stroke (US 2014/0371161). Peptide LPDYYDTPL (SEQ ID NO:9), based upon the PDZ domain sequence of human PHLPP-1, has been shown to be useful in the production of anti-PHLPP1 antibodies (Jackson, et al. (April 2015) *Sci. Rep.* 5:9377). Further, peptides having the sequence REPRIL-SEEEQEMFRDFDYIADWC (SEQ ID NO:208) have been suggested for use in treating cancer, stroke and myocardial infarction (US 2007/0196883).

SUMMARY OF THE INVENTION

This invention provides a modified peptide composed of a PDZ binding domain consisting of SEQ ID NO:1 and (a) between one and three additional non-native N-terminal amino acid residues, (b) between one and three additional non-native C-terminal amino acid residues, (c) a post-translational modification, (d) introduction of one or more nonhydrolyzable bonds, or (e) a combination of one or more of (a) to (d). This invention also provides a modified peptide composed of a PDZ binding domain consisting of SEQ ID NO:2 or a PDK1 interacting fragment consisting of SEQ ID NO:3 and (a) between one and 50 additional non-native amino acid residues, (b) one or more post-translational modifications, (c) introduction of one or more nonhydrolyzable bonds, or (d) a combination of one or more of (a) to (c). In some embodiments of the modified peptide, the additional non-native amino acid residues constitute a cell-penetrating peptide. Pharmaceutical compositions containing the modified peptide, a pharmaceutically acceptable carrier, and optionally nicotinamide are also provided. Further, modified peptides comprising the amino acid sequence of SEQ ID NO: 63-110, 118-134, or 142-206 are further provided.

This invention also provides a method for treating sudden cardiac arrest by administering to a subject in cardiac arrest a modified peptide composed of a PDZ binding domain consisting of SEQ ID NO:1 or SEQ ID NO:2, or a PDK1 interacting fragment consisting of SEQ ID NO:3 and (a) between one and 50 additional non-native amino acid residues, (b) one or more post-translational modifications, (c) introduction of one or more nonhydrolyzable bonds, (d) a combination of one or more of (a) to (c), thereby treating the subject's cardiac arrest. In one embodiment, the additional non-native amino acid residues constitute a cell-penetrating peptide. In another embodiment, the modified peptide is administered with a pharmaceutically acceptable carrier. In a further embodiment, the method further includes the administration of nicotinamide. In yet another embodiment, the modified peptide is administered to the subject after heart function is restored. In further embodiments, the nicotinamide is administered during cardiopulmonary resuscitation and the modified peptide is administered to the subject after heart function is restored; the nicotinamide and modified peptide are administered to the subject after heart function is restored; or the nicotinamide and modified peptide are administered during cardiopulmonary resuscitation. In still other embodiments, the method includes the prestep of determining the level of sorbitol or taurine in a blood sample from the subject, wherein an elevated level of sorbitol or taurine in the blood sample from the subject as compared to a control sample indicates the amount of modified peptide to administer to the subject.

A kit for treating cardiac arrest is also provided. The kit of the invention includes (a) a modified peptide comprising a PDZ binding domain consisting of SEQ ID NO:1 or SEQ ID NO:2, or a PDK1 interacting fragment consisting of SEQ ID NO:3 and (i) between one and 50 additional non-native amino acid residues, (ii) one or more post-translational modifications, (iii) introduction of one or more nonhydrolyzable bonds, (iv) a combination of one or more of (i) to (iii); and (b) nicotinamide, one or more reagents for detecting sorbitol, one or more reagents for detecting taurine, or a combination thereof. In some embodiments, the additional non-native amino acid residues comprise a cell-penetrating peptide.

The invention further provides a method for guiding treatment of cardiac arrest. This method of the invention involves the steps of obtaining a blood sample from a subject suspected of being in cardiac arrest; contacting the blood sample with a reagent for detecting sorbitol or taurine; and determining the level of sorbitol or taurine in the blood sample as compared to a control sample, wherein an elevated level of sorbitol or taurine in the subject's sample as compared to the control sample indicates that the subject is in need of treatment with therapeutic hypothermia, nicotinamide, a modified PDZ binding domain peptide or a combination thereof.

DETAILED DESCRIPTION OF THE INVENTION

Figure 1A:
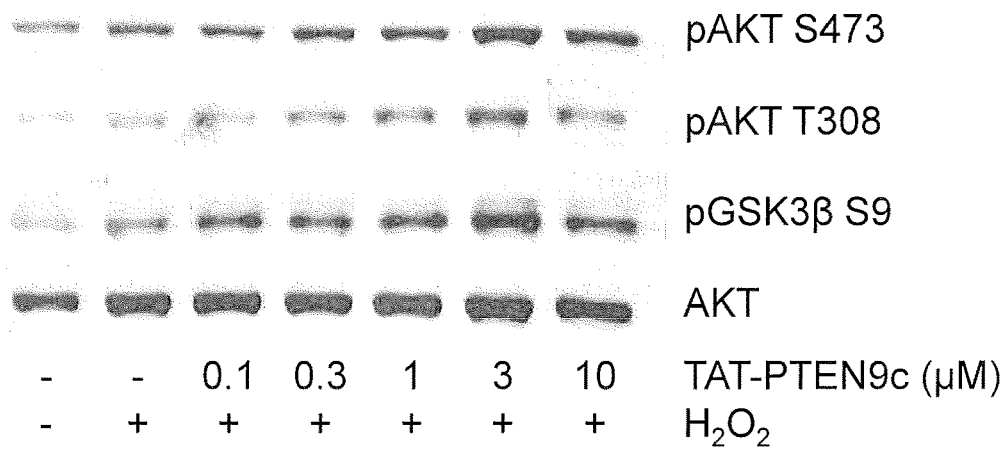
FIGS. 1A-1C show that TAT-PTEN9c peptide enhances Akt activation in response to $H_2O_2$ (FIG. 1A) or IGF-1 (FIG. 1B) in a concentration-dependent manner, wherein activation occurs within 10 minutes after administration (FIG. 1C).

Based upon genomic screening of active cooling protection in the mouse, as well as additional studies of knockout mice that do not respond to cooling, PTEN inhibition and activation of Akt have been identified as critical targets for cardiac arrest survival. Accordingly, a series of peptides that transiently and specifically inhibit proteins that regulate the Akt pathway have been developed for treating sudden cardiac arrest and increasing survival. In particular, modified peptides based upon the C-terminally localized PDZ binding domains of PTEN, PHLPP and PDK1 interacting fragment of PKN2 are described herein for use in interfering with endogenous PTEN, PHLPP and PKN2 binding to their adaptors resulting in increased Akt activation, causing Akt-enhanced glucose utilization (with decreased diversion of glucose via the alternate polyol pathway to sorbitol), and improved survival after sudden cardiac arrest.

The peptides of the invention are modified versions of PDZ binding domains of PTEN or PHLPP1 having the sequences Asp/Asn-Gln-His-Ser/Thr-Gln-Ile-Thr-Lys-Val (B-Q-H-S/T-Q-I-T-K-V; SEQ ID NO:1) or Leu-Pro-Asp/Asn-Cys/Tyr-Tyr-Asp/Asn-Thr-Pro-Leu (L-P-B-C/Y-Y-B-T-P-L; SEQ ID NO:2), respectively; or PDK1 interacting fragments or PKN2 having the sequence Phe-Arg/His-Asp/Asn-Phe-Asp/Asn-Tyr-Ile/Val-Ala-Asp/Asn (F-R/H-B-F-B-Y-I/V-A-B), SEQ ID NO:3). The term "modified" means a peptide having PTEN, PHLPP or PKN2 inhibitory activity, which has the amino acid sequence of SEQ ID NO:1, SEQ ID NO:2 or SEQ ID NO:3 and further includes the presence of one or more additional non-native amino acid residues at the C- and/or N-terminus, one or more nonhydrolyzable bonds and/or one or more post-translational modifications.

PDZ binding domains of PTEN having the amino acid sequence of Asp/Asn-Gln-His-Ser/Thr-Gln-Ile-Thr-Lys-Val (B-Q-H-S/T-Q-I-T-K-V; SEQ ID NO:1) include DQHSQ-ITKV (SEQ ID NO:4), DQHTQITKV (SEQ ID NO:5), NQHSQITKV (SEQ ID NO:6) and NQHTQITKV (SEQ ID NO:7).

PDZ binding domains of PHLPP1 having the amino acid sequence of Leu-Pro-Asp/Asn-Cys/Tyr-Tyr-Asp/Asn-Thr-Pro-Leu (L-P-B-C/Y-Y-B-T-P-L; SEQ ID NO:2) include LPDCYDTPL (SEQ ID NO:8), LPDYYDTPL (SEQ ID NO:9), LPNCYDTPL (SEQ ID NO:10), LPNYYDTPL (SEQ ID NO:11), LPDCYNTPL (SEQ ID NO:12), LPDYYNTPL (SEQ ID NO:13), LPNCYNTPL (SEQ ID NO:14) and LPNYYNTPL (SEQ ID NO:15).

PDK1 interacting fragments of PKN2 having the amino acid sequence of Phe-Arg/His-Asp/Asn-Phe-Asp/Asn-Tyr-Ile/Val-Ala-Asp/Asn (F-R/H-B-F-B-Y-I/V-A-B), SEQ ID NO:3) include FHDFDYVAD (SEQ ID NO:16), FRDFDY-IAD (SEQ ID NO:17), FHNFDYVAD (SEQ ID NO:18), FRNFDYIAD (SEQ ID NO:19), FHDFNYVAD (SEQ ID NO:20), FRDFNYIAD (SEQ ID NO:21), FHDFDYVAN (SEQ ID NO:22), FRDFDYIAN (SEQ ID NO:23), FHNF-NYVAD (SEQ ID NO:24), FRNFNYIAD (SEQ ID NO:25), FHNFDYVAN (SEQ ID NO:26), FRNFDYIAN (SEQ ID NO:27), FHDFNYVAN (SEQ ID NO:28), and FRDFNY-IAN (SEQ ID NO:29).

While the PDZ binding domains and PDK1 interacting fragment disclosed herein are derived from human and rodent sequences (i.e., mouse and/or rat), orthologs or allelic variants of the PDZ binding domains and PDK1 interacting fragment of PKN2 disclosed herein can also be used. The term "ortholog" refers to the same protein in another species, which exhibits the same activity. By comparison, "allelic variant" refers the same protein in the same species, which may have an altered amino acid sequence resulting from a polymorphism within the population. In certain embodiments, the PDZ binding domain or PDK1 interacting fragment ortholog or allelic variant has sequence identity of at least 80%, at least 85%, at least 90%, at least 95%, at least 96%, at least 97%, at least 98%, or at least 99%, but less than 100%, to the PDZ binding domains disclosed herein.

One feature of this invention involves the addition of one or more non-native amino acid residues to the N-terminus and/or C-terminus of a PDZ binding domain or PDK1 interacting fragment disclosed herein. "Non-native amino acid residues" refers to residues not naturally associated with the N-terminus or C-terminus of the PDZ binding domain or PDK1 interacting fragment. For example, the PDZ binding domain of human PTEN is found in the context of the following amino acid sequence of PTEN: NEPFDE DQHTQITKV (SEQ ID NO:30). Accordingly, the addition of a glycine to the N-terminus of the PDZ binding domain DQHTQITKV (SEQ ID NO:5) is considered the addition of a non-native amino acid residue. In some embodiments, between one and 50 additional non-native amino acid residues are added to the PDZ binding domain or PDK1 interacting fragment. In other embodiments, between one and 40, one and 35, one and 30, one and 25, one and 20, one and 15, or one and 10 additional non-native amino acid residues are added to the PDZ binding domain or PDK1 interacting fragment. In particular embodiments, 1, 2, 3, 4, 5, 6, 7, 8, 9, 10, 11, 12, 13, 14, 15, 16, 17, 18, 19 or 20 additional non-native amino acid residues are added to the PDZ binding domain or PDK1 interacting fragment. In some embodiments, one or more of glycine, asparagine, aspartic acid, cysteine, or tryptophan are added to the N-terminus of the PDZ binding domain or PDK1 interacting fragment. In other embodiments, one or more of methionine, alanine, arginine, valine, lysine or glutamine are added to the C-terminus.

In certain embodiments, the one or more non-native amino acid residues added to the PDZ binding domain or PDK1 interacting fragment constitute a protein transduction domain (PTD) or cell-penetrating peptide (CPP) that is highly rich in basic residues. CPPs can be divided into three classes, protein-derived peptides, model peptides and designed peptides. Protein-derived peptides are the short stretches of the protein domain that are primarily responsible for the translocation ability, also called PTDs. Examples include TAT peptide derived from the 86-mer TAT protein, penetratin derived from homeodomain of Drosophila Antennapedia, pVEC derived from murine vascular endothelial cadherin, and signal sequence-based peptides or membrane translocating sequences (MTSs). Model peptides such as MAP (KLALKLALKALKAALKLA; SEQ ID NO:31) are CPPs that mimic the translocation properties of known CPPs. Designed CPPs encompass the chimeric peptides that are produced by the fusion of hydrophilic and hydrophobic domains from different sources. Examples of designed CPPs include transportan (a fusion of galanin and mastoparan), MPG (a chimeric peptide composed of the fusion sequence of HIV-1 gp41 protein and the nuclear localization sequence of SV40 T-antigen). In addition, synthetic peptides such as polyarginines also exhibit translocation. In some embodiments, the CPP is a short peptide, preferably of less than 40 amino acid residues in length. In other embodiments, the CPP is added to the N-terminus of the PDZ binding domain.

In particular embodiments, the PDZ binding domain or PDK1 interacting fragment is conjugated or linked to a CPP having the sequence comprising or consisting of:

(a) $X_1$-K-K-K-I-K-$\psi$-E-I-$X_2$-$X_3$ (SEQ ID NO:32), wherein $X_1$ is K, V-K or is absent; $X_2$ is K, K-I or absent; $X_3$ is a sequence of 1 to 4 amino acid residues or is absent; and $\psi$ is any amino acid residue, wherein specific examples of (a) include, but are not limited to, VKKKKIKREIKI (SEQ ID NO:33), VKKKKIKNEIKI (SEQ ID NO:34), VKKK-KIKAEIKI (SEQ ID NO:35) or VKKKKIKKEIKI (SEQ ID NO:36);

(b) (RQKRLI)$_3$ (SEQ ID NO:37), (RHSRIG)$_3$ (SEQ ID NO:38), RHSRIGIIQQRRTRNG (SEQ ID NO:39), RHSRIGVTRQRRARNG (SEQ ID NO:40), or RRRRRRRSRGRRRTY (SEQ ID NO:41); or (c) a CPP listed in Table 1.

TABLE 1

| CPP | Sequence | SEQ ID NO: |
|---|---|---|
| Tat peptide | RKKRRQRRR | 42 |
| | YGRKKRRQRRR | 43 |
| Polyarginine peptide | RRRRRRRRR | 44 |
| | RRRRRRRRRR | 45 |
| HA2-R$_9$ | GLFEAIEGFIENGWEGMIDGWYGRRRRRRRRR | 46 |
| Penetratin peptide | RQIKIWFQNRRMKWKK | 47 |
| Transportan peptide | GWTLNSAGYLLGKINLKALAALAKKIL | 48 |
| Maurocalcine peptide | GDCLPHLKLCKENKDCCSKKCKRRGTNIEKRCR | 49 |
| Polylysine peptide | KKKKKKKKKK | 50 |
| | KKKKKKKKK | 51 |
| HIV-Tat derived PTD4 peptide | YARAAARQARA | 52 |
| Hepatitis B virus translocation motif | PLSSIFSRIGDP | 53 |
| mPrP$_{1-28}$ peptide | MANLGYWLLALFVMWTDVGLCKKRPKP | 54 |
| POD peptide | GGG(ARKKAAKA)$_4$ | 55 |
| pVEC peptide | LLIILRRRRIRKQAHAHSK | 56 |
| EB 1 peptide | LIRLWSHLIHIWFQNRRLKWKKK | 57 |
| Rath peptide | TPWWRLWTKWHHKRRDLPRKPE | 58 |
| CADY peptide | GLWRALWRLLRSLWRLLWRA | 59 |
| Histatin 5 peptide | DSHAKRHHGYRKFHEKHHSHRGY | 60 |
| Cyt$_{86-101}$ peptide | KKKEERADLIAYLKKA | 61 |
| sC18 | GLRKRLRKFRNKIKEK | 62 |

The cell-penetrating peptide may further be one described in US 2013/0129726; WO 03/011898; WO 2004/011595; WO 2010/112471; WO 2012/042038; WO 2013/098337; Guergnon, et al. (2006) *Mol. Pharmacol.* 69:1115-1124; Fonseca, et al. (2009) *Adv. Drug Deliv. Rev.* 61:953-964; Nakase, et al. (2012) *J. Contr. Rel.* 159:181-188; Bolhassani (2011) *Biochim. Biophys. Acta* 1816:232-246; Milleti (2012) *Drug Disc. Today* 17:850-860; or Aroui et al. (2009) *Cancer Lett.* 285:28-38. In addition, dimerization of CPPs such as sC18 has been shown to increase the drug-delivery potential of the CPP (Hoyer, et al. (2012) *Beilstein J. Org. Chem.* 8:1788-97).

In certain embodiments, the PDZ binding domain or PDK1 interacting fragment is conjugated or linked to a Tat peptide, polyarginine peptide, or polylysine peptide. In one embodiment, the PDZ binding domain or PDK1 interacting fragment is conjugated or linked to a Tat peptide having the amino acid sequence YGRKKRRQRRR (SEQ ID NO:43). In another embodiment, the PDZ binding domain or PDK1 interacting fragment is conjugated or linked to a polyarginine peptide having amino acid sequence RRRRRRRRR (SEQ ID NO:44). In a further embodiment, the PDZ binding domain or PDK1 interacting fragment is conjugated or linked to a polylysine peptide having the amino acid sequence KKKKKKKKK (SEQ ID NO:51).

Alternatively, or in addition to one or more additional non-native amino acid residues, the modified peptide of the invention includes one or more post-translational modifications. Such modifications can be used to increase stability, half-life, uptake, activity or efficacy of the modified peptide. Known modifications include, but are not limited to, acetylation, acylation, amidation, covalent attachment of a nucleotide or nucleotide derivative, covalent attachment of a lipid or lipid derivative, covalent attachment of phosphatidylinositol, cross-linking, cyclization, disulfide bond formation, formation of covalent crosslinks, formation of cystine, formation of pyroglutamate, formylation, glycosylation, GPI anchor formation, hydroxylation, methylation, myristoylation, oxidation, phosphorylation, prenylation, racemization, selenoylation, sulfation, and ubiquitination.

Modifications can occur anywhere in the modified peptide, including the peptide backbone, the amino acid side-chains and/or the N- or C-terminus. A brief description of various post-translational modifications within the scope of this invention is set forth in Table 2.

TABLE 2

| Protein Modification | Description |
|---|---|
| Acetylation | Acetylation of N-terminus or ε-lysines. Introducing an acetyl group into a protein, specifically, the substitution of an acetyl group for an active hydrogen atom. A reaction involving the replacement of the hydrogen atom of a hydroxyl group with an acetyl group ($CH_3CO$) yields a specific ester, the acetate. Acetic anhydride is commonly used as an acetylating agent, which reacts with free hydroxyl groups. Acylation may facilitate addition of other functional groups. A common reaction is acylation of, e.g., conserved lysine residues with a biotin appendage. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Amidation is the addition of an amide group to the end of the polypeptide chain. The amide group for C-terminal amidation may be contributed by a glycine residue. |
| Carbamylation | Carbamylation represents a useful reaction for the reversible blocking of tyrosine hydroxyl groups, the O-carbamyl substituent being readily removed by hydrolysis at neutral and alkaline pH values. The reaction involves nucleophilic addition of the amino or phenoxide group to the molecular form of cyanic acid. |
| Carboxylation | Carboxylation is a modification of glutamate residues to γ-carboxyglutamate. |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Attachment of a nucleotide or nucleotide derivative | May be used as a tag or as a basis for further derivatizing a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy) ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in peptides are formed by thiol-disulfide exchange reactions, particularly between cysteine residues (e.g., formation of cystine). |
| Formylation | The addition of a formyl group to, e.g., the N-terminus of a protein. See, e.g., U.S. Pat. No. 4,059,589, U.S. Pat. No. 4,801,742, and U.S. Pat. No. 6,350,902. |
| Glycosylation | Glycosylation may be used to add saccharides (or polysaccharides) to the hydroxy oxygen atoms of serine and threonine side chains (which is also known as O-linked glycosylation). Glycosylation may also be used to add saccharides (or polysaccharides) to the amide nitrogen of asparagine side chains (which is also known as N-linked glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group linked through a carbohydrate containing linker (e.g., glucosamine and mannose linked to phosphoryl ethanolamine residue) to the C-terminal amino acid of a peptide. |
| Hydroxylation | Chemical process that introduces one or more hydroxyl groups (—OH) into a peptide (or radical). Hydroxylation reactions are typically catalyzed by hydroxylases. Proline is the principal residue to be hydroxylated in proteins, which occurs at the $C^\gamma$ atom, forming hydroxyproline (Hyp). In some cases, proline may be hydroxylated at its $C^\beta$ atom. Lysine may also be hydroxylated on its $C^\delta$ atom, forming hydroxy lysine (Hyl). These three reactions are catalyzed by large, multi-subunit enzymes known as prolyl 4-hydroxylase, prolyl 3-hydroxylase and lysyl 5-hydroxylase, respectively. |
| ISGylation | Covalently linking a peptide to the ISG15 (Interferon-Stimulated Gene 15) protein, for, e.g., modulating immune response. |
| Methylation | Methylation of proteins occurs on nitrogens and oxygens. The activated methyl donor for these reactions is S-adenosylmethionine (SAM). The most common methylations are on the ε-amine of the R-group of lysine residues and the guanidino moiety of the R-group of arginine. Additional nitrogen methylations are found on the imidazole ring of histidine and the R-group amides of glutamate and aspartate. Methylation of the oxygen of the R-group carboxylates of glutamate and aspartate also takes place and forms methyl esters. Proteins can also be methylated on the thiol R-group of cysteine. |
| Myristoylation | Myristoylation involves the covalent attachment of a myristoyl group (a derivative of myristic acid), via an amide bond, to the alpha-amino group of an N-terminal residue. This addition is catalyzed by the N-myristoyltransferase enzyme. |
| Oxidation | Oxidation of cysteines. Oxidation of N-terminal Serine or Threonine residues Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| Polyglutamylation | Polyglutamylation occurs at the glutamate residues of a protein. The gamma-carboxy group of a glutamate will form a peptide-like bond with the amino group of a free glutamate whose alpha-carboxy group may be extended into a polyglutamate chain. The glutamylation reaction is catalyzed by a |

TABLE 2-continued

| Protein Modification | Description |
| --- | --- |
|  | glutamylase enzyme (or removed by a deglutamylase enzyme). Polyglutamylation can be carried out at the C-terminus of proteins to add up to about six glutamate residues. |
| Phosphopantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed, e.g., in U.S. Pat. No. 4,534,894. Typically, phosphorylation occurs at the serine, threonine, and tyrosine residues of a protein. |
| Prenylation | Prenylation (or isoprenylation or lipidation) is the addition of hydrophobic molecules to a protein. Protein prenylation involves the transfer of either a farnesyl (linear grouping of three isoprene units) or a geranyl-geranyl moiety to C-terminal cysteine(s) of the target peptide. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |
| Sulfation | Processes for sulfating hydroxyl moieties, particularly tertiary amines, are described in, e.g., U.S. Pat. No. 6,452,035. A process for sulfation of a protein or peptide by contacting the protein or peptide with sulphuric acid in the presence of a non-aqueous apolar organic solvent and contacting the resultant solution with a dehydrating agent is disclosed. |
| sulfonation | Sulfonation refers to the transfer of the sulfonate group ($SO_3^{-1}$) from 3'-phosphoadenosine-5'-phosphosulfate (PAPS), and can occur through several types of linkages, such as esters and anhydrides (O-sulfonation), amides (N-sulfonation), and thioesters (S-sulfonation), of which O-sulfonation is the most prominent. The transfer of $SO_3^{-1}$ to a hydroxyl or phenolic acceptor (O-sulfonation) generates a sulfono-derivative. |
| SUMOylation | Covalently linking SUMO (small ubiquitin-related modifier) to lysine of a peptide, for, e.g., stabilizing the peptide. SUMOylation is described in US 2014/0234287. |
| Transglutamination | Reaction where γ-glutaminyl of a glutamine residue from a peptide is transferred to a primary amine or the ε-amino group of lysine. |
| Ubiquitination | Covalent linkage of ubiquitin to, e.g., lysine residues of a protein. |

In certain embodiments, the C-terminus of the PDZ binding domain or PDK1 interacting fragment may be modified with amidation (denoted by —NH$_2$), addition of peptide alcohols and aldehydes, addition of esters, addition of p-nitroaniline or thioesters. In other embodiments, the N-terminus of the PDZ binding domain/PDK1 interacting fragment and/or side chains may be modified by PEGylation, acetylation, formylation, addition of a fatty acid, addition of benzoyl, addition of bromoacetyl, addition of pyroglutamyl, succinylation, addition of tetrabutyoxycarbonyl and addition of 3-mercaptopropyl, acylations (e.g., lipopeptides), biotinylation, phosphorylation, sulfation, glycosylation, introduction of maleimido group, chelating moieties, chromophores and fluorophores. In an embodiment, the peptide is conjugated to a fatty acid, e.g., the peptide is myristoylated (denoted by "myr". For example, a fatty acid may be conjugated to the N-terminus of the PDZ binding domain or PDK1 interacting fragment, such fatty acids include caprylic acid, capric acid, lauric acid, myristic acid, palmitic acid, stearic acid, etc. Furthermore, cysteines in peptides can be palmitoylated. In an embodiment, the PDZ binding domain is myristylated, stearylated or palmitoylated at the N-terminal amino acid residue. In an embodiment, the PDZ binding domain is myristylated at the N-terminal amino acid residue.

Alternatively, or in addition to one or more additional non-native amino acid residues and post-translational modifications, the modified peptide of the invention includes the introduction of one or more nonhydrolyzable bonds to protect the peptide from proteolysis. Such modifications include internal modifications such as the replacement of at least one —CONH-peptide bond by a (CH$_2$NH) reduced bond, a (NHCO) retro-inverso bond, a (CH$_2$—O) methylene-oxy bond, a (CH$_2$—S) thiomethylene bond, a (CH$_2$CH$_2$) carba bond, a (CO—CH) cetomethylene bond, a (CHOH—CH$_2$) hydroxyethylene bond, a (N—N) bond, a E-alcene bond, or a —CH—CH— bond.

The modified peptide of the invention can include one or more additional non-native amino acid residues, one or more post-translational modifications, and/or one or more nonhydrolyzable bonds. Representative modified peptides including PDZ binding domains of PTEN and PHLPP and PDK1 interacting fragments of PKN include, but are not limited to, the peptides listed in Table 3.

TABLE 3

| Peptide Sequence | SEQ ID NO: |
| --- | --- |
| YGRKKRRQRRRLPDCYDTPL | 63 |
| RRRRRRRRRLPDCYDTPL | 64 |
| KKKKKKKKKLPDCYDTPL | 65 |
| YGRKKRRQRRRLPDCYDTPL-NH$_2$ | 66 |
| RRRRRRRRRLPDCYDTPL-NH$_2$ | 67 |
| KKKKKKKKKLPDCYDTPL-NH$_2$ | 68 |
| myr-LPDCYDTPL | 69 |
| LPDCYDTPL-NH$_2$ | 70 |
| myr-LPDCYDTPL-NH$_2$ | 71 |
| myr-GLPDCYDTPL | 72 |
| GLPDCYDTPL-NH$_2$ | 73 |
| myr-GLPDCYDTPL-NH$_2$ | 74 |
| YGRKKRRQRRRLPNCYNTPL | 75 |
| RRRRRRRRRLPNCYNTPL | 76 |
| KKKKKKKKKLPNCYNTPL | 77 |
| YGRKKRRQRRRLPNCYNTPL-NH$_2$ | 78 |
| RRRRRRRRRLPNCYNTPL-NH$_2$ | 79 |
| KKKKKKKKKLPNCYNTPL-NH$_2$ | 80 |
| LPNCYNTPL-NH$_2$ | 81 |

TABLE 3-continued

| Peptide Sequence | SEQ ID NO: |
|---|---|
| myr-LPNCYNTPL-NH₂ | 82 |
| myr-LPNCYNTPL | 83 |
| GLPNCYNTPL-NH₂ | 84 |
| myr-GLPNCYNTPL-NH₂ | 85 |
| myr-GLPNCYNTPL | 86 |
| YGRKKRRQRRRLPDYYDTPL | 87 |
| RRRRRRRRRLPDYYDTPL | 88 |
| KKKKKKKKKLPDYYDTPL | 89 |
| YGRKKRRQRRRLPDYYDTPL-NH₂ | 90 |
| RRRRRRRRRLPDYYDTPL-NH₂ | 91 |
| KKKKKKKKKLPDYYDTPL-NH₂ | 92 |
| LPDYYDTPL-NH₂ | 93 |
| myr-LPDYYDTPL-NH₂ | 94 |
| myr-LPDYYDTPL | 95 |
| GLPDYYDTPL-NH₂ | 96 |
| myr-GLPDYYDTPL-NH₂ | 97 |
| myr-GLPDYYDTPL | 98 |
| YGRKKRRQRRRLPNYYNTPL | 99 |
| RRRRRRRRRLPNYYNTPL | 100 |
| KKKKKKKKKLPNYYNTPL | 101 |
| YGRKKRRQRRRLPNYYNTPL-NH₂ | 102 |
| RRRRRRRRRLPNYYNTPL-NH₂ | 103 |
| KKKKKKKKKLPNYYNTPL-NH₂ | 104 |
| LPNYYNTPL-NH₂ | 105 |
| myr-LPNYYNTPL-NH₂ | 106 |
| myr-LPNYYNTPL | 107 |
| GLPNYYNTPL-NH₂ | 108 |
| myr-GLPNYYNTPL-NH₂ | 109 |
| myr-GLPNYYNTPL | 110 |
| YGRKKRRQRRRDQHSQITKV | 111 |
| RRRRRRRRRDQHSQITKV | 112 |
| KKKKKKKKKDQHSQITKV | 113 |
| YGRKKRRQRRRDQHSQITKV-NH₂ | 114 |
| RRRRRRRRRDQHSQITKV-NH₂ | 115 |
| KKKKKKKKKDQHSQITKV-NH₂ | 116 |
| DQHSQITKV-NH₂ | 117 |
| myr-DQHSQITKV-NH₂ | 118 |
| myr-DQHSQITKV | 119 |
| GDQHSQITKV-NH₂ | 120 |

TABLE 3-continued

| Peptide Sequence | SEQ ID NO: |
|---|---|
| myr-GDQHSQITKV-NH₂ | 121 |
| myr-GDQHSQITKV | 122 |
| YGRKKRRQRRRNQHSQITKV | 123 |
| RRRRRRRRRNQHSQITKV | 124 |
| KKKKKKKKKNQHSQITKV | 125 |
| YGRKKRRQRRRNQHSQITKV-NH₂ | 126 |
| RRRRRRRRRNQHSQITKV-NH₂ | 127 |
| KKKKKKKKKNQHSQITKV-NH₂ | 128 |
| NQHSQITKV-NH₂ | 129 |
| myr-NQHSQITKV-NH₂ | 130 |
| myr-NQHSQITKV | 131 |
| GNQHSQITKV-NH₂ | 132 |
| myr-GNQHSQITKV-NH₂ | 133 |
| myr-GNQHSQITKV | 134 |
| YGRKKRRQRRRDQHTQITKV | 135 |
| RRRRRRRRRDQHTQITKV | 136 |
| KKKKKKKKKDQHTQITKV | 137 |
| YGRKKRRQRRRDQHTQITKV-NH₂ | 138 |
| RRRRRRRRRDQHTQITKV-NH₂ | 139 |
| KKKKKKKKKDQHTQITKV-NH₂ | 140 |
| DQHTQITKV-NH₂ | 141 |
| myr-DQHTQITKVV-NH₂ | 142 |
| myr-DQHTQITKV | 143 |
| GDQHTQITKV-NH₂ | 144 |
| myr-GDQHTQITKV-NH₂ | 145 |
| myr-GDQHTQITKV | 146 |
| YGRKKRRQRRRNQHTQITKV | 147 |
| RRRRRRRRRNQHTQITKV | 148 |
| KKKKKKKKKNQHTQITKV | 149 |
| YGRKKRRQRRRNQHTQITKV-NH₂ | 150 |
| RRRRRRRRRNQHTQITKV-NH₂ | 151 |
| KKKKKKKKKNQHTQITKV-NH₂ | 152 |
| NQHTQITKV-NH₂ | 153 |
| myr-NQHTQITKV-NH₂ | 154 |
| myr-NQHTQITKV | 155 |
| GNQHTQITKV-NH₂ | 156 |
| myr-GNQHTQITKV-NH₂ | 157 |
| myr-GNQHSQITKV | 158 |

TABLE 3-continued

| Peptide Sequence | SEQ ID NO: |
|---|---|
| YGRKKRRQRRRFHDFDYVAD | 159 |
| RRRRRRRRRFHDFDYVAD | 160 |
| KKKKKKKKKFHDFDYVAD | 161 |
| YGRKKRRQRRRFHDFDYVAD-NH$_2$ | 162 |
| RRRRRRRRRFHDFDYVAD-NH$_2$ | 163 |
| KKKKKKKKKFHDFDYVAD-NH$_2$ | 164 |
| FHDFDYVAD-NH$_2$ | 165 |
| myr-FHDFDYVAD-NH$_2$ | 166 |
| myr-FHDFDYVAD | 167 |
| GFHDFDYVAD-NH$_2$ | 168 |
| myr-GFHDFDYVAD-NH$_2$ | 169 |
| myr-GFHDFDYVAD | 170 |
| YGRKKRRQRRRFHNFNYVAN | 171 |
| RRRRRRRRRFHNFNYVAN | 172 |
| KKKKKKKKKFHNFNYVAN | 173 |
| YGRKKRRQRRRFHNFNYVAN-NH$_2$ | 174 |
| RRRRRRRRRFHNFNYVAN-NH$_2$ | 175 |
| KKKKKKKKKFHNFNYVAN-NH$_2$ | 176 |
| FHNFNYVAN-NH$_2$ | 177 |
| myr-FHNFNYVAN-NH$_2$ | 178 |
| myr-FHNFNYVAN | 179 |
| GFHNFNYVAN-NH$_2$ | 180 |
| myr-GFHNFNYVAN-NH$_2$ | 181 |
| myr-GFHNFNYVAN | 182 |
| YGRKKRRQRRRFRDFDYIAD | 183 |
| RRRRRRRRRFRDFDYIAD | 184 |
| KKKKKKKKKFRDFDYIAD | 185 |
| YGRKKRRQRRRFRDFDYIAD-NH$_2$ | 186 |
| RRRRRRRRRFRDFDYIAD-NH$_2$ | 187 |
| KKKKKKKKKFRDFDYIAD-NH$_2$ | 188 |
| FRDFDYIAD-NH$_2$ | 189 |
| myr-FRDFDYIAD-NH$_2$ | 190 |
| myr-FRDFDYIAD | 191 |
| GFRDFDYIAD-NH$_2$ | 192 |
| myr-GFRDFDYIAD-NH$_2$ | 193 |
| myr-GFRDFDYIAD | 194 |
| YGRKKRRQRRRFRNFNYIAN | 195 |
| RRRRRRRRRFRNFNYIAN | 196 |
| KKKKKKKKKFRNFNYIAN | 197 |

TABLE 3-continued

| Peptide Sequence | SEQ ID NO: |
|---|---|
| YGRKKRRQRRRFRNFNYIAN-NH$_2$ | 198 |
| RRRRRRRRRFRNFNYIAN-NH$_2$ | 199 |
| KKKKKKKKKFRNFNYIAN-NH$_2$ | 200 |
| FRNFNYIAN-NH$_2$ | 201 |
| myr-FRNFNYIAN-NH$_2$ | 202 |
| myr-FRNFNYIAN | 203 |
| GFRNFNYIAN-NH$_2$ | 204 |
| myr-GFRNFNYIAN-NH$_2$ | 205 |
| myr-GFRNFNYIAN | 206 |

In some embodiments, the modified peptide has the amino acid sequence of SEQ ID NO:63-206. In other embodiments, the modified peptide of the invention has the amino acid sequence of SEQ ID NO:63-110, 118-134, or 142-206. In one embodiment, the modified peptide of the invention is selected from YGRKKRRQRRRDQHSQITKV (SEQ ID NO:111), RRRRRRRRRDQHSQITKV (SEQ ID NO:112), KKKKKKKKKDQHSQITKV (SEQ ID NO:113), YGRKKRRQRRRDQHSQITKV-NH$_2$ (SEQ ID NO:114), DQHSQITKV-NH$_2$ (SEQ ID NO:117), myr-DQHSQITKV-NH$_2$ (SEQ ID NO:118), myr-DQHSQITKV (SEQ ID NO:119), GDQHSQITKV-NH$_2$ (SEQ ID NO:120), myr-GDQHSQITKV-NH$_2$ (SEQ ID NO:121), myr-GDQHSQITKV (SEQ ID NO:122), YGRKKRRQRRRDQHTQITKV (SEQ ID NO:135), RRRRRRRRRDQHTQITKV (SEQ ID NO:136), KKKKKKKKKDQHTQITKV (SEQ ID NO:137), YGRKKRRQRRRDQHTQITKV-NH$_2$ (SEQ ID NO:138), RRRRRRRRRDQHTQITKV-NH$_2$ (SEQ ID NO:139), KKKKKKKKKDQHTQITKV-NH$_2$ (SEQ ID NO:140), DQHTQITKV-NH$_2$ (SEQ ID NO:141), myr-DQHTQITKVV-NH$_2$ (SEQ ID NO:142), myr-DQHTQITKV (SEQ ID NO:143), GDQHTQITKV-NH$_2$ (SEQ ID NO:144), myr-GDQHTQITKV-NH$_2$ (SEQ ID NO:145), and myr-GDQHTQITKV (SEQ ID NO:146).

The modified peptide of the invention can be synthesized recombinantly using recombinant DNA techniques. Thus, the invention provides polynucleotides that encode the modified peptides of the invention. In a related aspect, the invention provides vectors, particularly expression vectors that comprise the polynucleotides encoding the modified peptides of the invention. In certain embodiments, the vector provides replication, transcription and/or translation regulatory sequences that facilitate recombinant synthesis of the desired peptides in a eukaryotic cell or prokaryotic cell. Accordingly, the invention also provides host cells for recombinant expression of the peptides and methods of harvesting and purifying the peptides produced by the host cells. Production and purification of recombinant peptides is a routine practice to one of skilled in the art and any suitable methodology can be used.

Alternatively, the modified peptide of the invention can be synthesized by any of the chemical synthesis techniques known in the art, particularly solid-phase synthesis techniques, for example, using commercially-available automated peptide synthesizers. See, for example, Stewart & Young (1984) *Solid Phase Peptide Synthesis*, 2$^{nd}$ ed., Pierce Chemical Co.; Tarn, et al. (1983) *J. Am. Chem. Soc.* 105:

6442-55; Merrifield (1986) *Science* 232:341-347; and Barany et al. (1987) *Int. J. Peptide Protein Res.* 30:705-739.

The modified peptide can be isolated and/or purified by any suitable methods known in the art including without limitation gel filtration and affinity purification. In some embodiments, the modified peptide is produced in the form of a fusion protein, such that the fusion moiety (or the epitope tag) can be used to isolate the modified peptide and optionally be cleaved off using a protease. In one aspect, the modified peptide is at least 1% pure, e.g., at least 5% pure, at least 10% pure, at least 20% pure, at least 40% pure, at least 60% pure, at least 80% pure, and at least 90% pure, as determined by SDS-PAGE. Once isolated and/or purified, the properties of the modified peptide can be readily verified by techniques known to those skilled in the art such as those described in the examples of the present application.

The modified peptides of this invention find application in treating sudden cardiac arrest and increasing cardiac arrest survival. Accordingly, this invention also provides a method for treating sudden cardiac arrest by administering to a subject in cardiac arrest one or more modified peptides including a PDZ binding domain consisting of SEQ ID NO:1, SEQ ID NO:2 or SEQ ID NO:3 and having (a) between one and 50 (e.g., between 1 and 3) additional non-native amino acid residues, (b) one or more post-translational modifications, (c) introduction of one or more nonhydrolyzable bonds, or (d) a combination of one or more of (a) to (c), thereby treating the subject's cardiac arrest.

For the purposes of this invention, "treating" a subject having a disease or disorder means accomplishing one or more of the following: (a) reducing the severity of the disease; (b) arresting the development of the disease or disorder; (c) inhibiting worsening of the disease or disorder; (d) limiting or preventing recurrence of the disease or disorder in patients that have previously had the disease or disorder; (e) causing regression of the disease or disorder; (f) improving or eliminating the symptoms of the disease or disorder; and (g) improving survival. In accordance with certain embodiments of this invention, "treating" preferably refers to a measurable increase in Akt activation, a decrease in glucose shunting to polyol pathway and an increase or improvement in the survival of a subject in cardiac arrest.

As used herein, the term "amount effective," "effective amount" or a "therapeutically effective amount" refers to an amount of the modified peptide of the invention or a pharmaceutical composition containing the inventive peptide sufficient to achieve the stated desired result. The amount of the modified peptide that constitutes an "effective amount" or "therapeutically effective amount" may vary depending on the severity of the disease, the condition, weight, or age of the patient to be treated, the frequency of dosing, or the route of administration, but can be determined routinely by one of ordinary skill in the art. A clinician may titer the dosage or route of administration to obtain the optimal therapeutic effect. Typical dosages range from about 0.1 µg/kg to up to about 100 mg/kg or more, depending on the factors mentioned above. In certain embodiments, the dosage may range from 0.1 µg/kg up to about 100 mg/kg, or 1 µg/kg up to about 100 mg/kg, or 5 µg/kg up to about 100 mg/kg.

In some embodiments, the subject in cardiac arrest is administered one or more modified peptides of the invention after heart function is restored. In other embodiments, the subject in cardiac arrest is administered one or more modified peptides of the invention in combination with cardiopulmonary resuscitation or defibrillation. In further embodiments, the subject in cardiac arrest is administered one or more modified peptides of the invention in combination with nicotinamide, wherein the nicotinamide is administered before, concurrently with, or after administration of the one or more modified peptides. In particular embodiments, the nicotinamide is administered before (e.g., during CPR) the administration of the one or more modified peptides. In other embodiments, the nicotinamide is administered during cardiopulmonary resuscitation and the modified peptide is administered to the subject after heart function is restored; the nicotinamide and modified peptide are administered to the subject after heart function is restored; or the nicotinamide and modified peptide are administered during cardiopulmonary resuscitation.

The modified peptides of the invention either alone or in combination with nicotinamide may be incorporated into a pharmaceutical composition comprising a pharmaceutically acceptable carrier or excipient. Optimal pharmaceutical compositions can be determined by one skilled in the art depending upon, for example, the intended route of administration, delivery format and desired dosage.

The dosage forms may also include the necessary physiologically acceptable carrier material, excipient, lubricant, buffer, surfactant, antibacterial, bulking agent (such as mannitol), antioxidants (ascorbic acid or sodium bisulfite) and the like.

Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20 and polysorbate 80, TRITON, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, *Remington's Pharmaceutical Sciences* (19th edition, 1995).

The primary vehicle or carrier in a pharmaceutical composition may be either aqueous or nonaqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can include Tris buffer of about pH 7.0-8.5, or acetate buffer of about pH 4.0-5.5, which may further include sorbitol or a suitable substitute thereof. Pharmaceutical compositions of the invention may be prepared for storage by mixing the selected composition having the desired degree of purity with optional formulation agents in the form of a lyophilized cake or an aqueous solution. Further, the modified peptides of the invention may be formulated as a lyophilizate using appropriate excipients such as sucrose.

Administration routes for the pharmaceutical compositions of the invention include injection by intravenous, intraperitoneal, intracerebral (intra-parenchymal), intracerebroventricular, intramuscular, intra-ocular, intraarterial, intraportal, or intralesional routes; by sustained release systems; or by implantation devices. Intranasal, oral and transdermal routes are also contemplates. Preferably, the pharmaceutical composition is administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The pharmaceutical compositions of the invention can be delivered parenterally. When parenteral administration is contemplated, the therapeutic compositions for use in this invention may be in the form of a pyrogen-free, parenterally acceptable aqueous solution comprising the desired compound identified in a screening method of the invention in a pharmaceutically acceptable vehicle. A particularly suitable vehicle for parenteral injection is sterile distilled water in which the compound is formulated as a sterile, isotonic solution, appropriately preserved. Preparation can involve the formulation of the desired molecule with an agent, such as injectable microspheres, bio-erodible particles, polymeric compounds, beads or liposomes, which may provide controlled or sustained release of the product which may then be delivered via a depot injection. Formulation with hyaluronic acid has the effect of promoting sustained duration in the circulation. Implantable drug delivery devices may be used to introduce the desired molecule.

To facilitate treatment in accordance with the present method, this invention also provides a companion diagnostic to guide the dosing of modified peptide needed to reverse metabolic injury. In particular, it has now been observed that elevated blood concentrations of sorbitol and taurine (2-aminoethanesulfonic acid) are associated with poor survival of SCA mice and SCA patients. In a mouse model of SCA, blood sorbitol and taurine concentrations were reduced by both active cooling during CPR as well as the administration of VO-OHpic. Thus, elevated blood concentrations of sorbitol and/or taurine reflect the metabolic recovery state of the heart during SCA and serve as diagnostic markers guiding treatment and predicting outcomes after SCA.

Accordingly, this invention also provides a method for guiding treatment of cardiac arrest with, e.g., a modified peptide of disclosed herein, hypothermia and/or nicotinamide. The method involves the steps of obtaining a blood sample from a subject suspected of having a cardiac arrest; contacting the blood sample with a reagent for detecting sorbitol or taurine; and determining the level of sorbitol or taurine in the blood sample as compared to a control sample, wherein elevated blood concentrations of sorbitol or taurine in the subject as compared to the control sample indicates that the subject is a candidate for treatment with one or more therapies including, but not limited to, therapeutic hypothermia, a modified PDZ binding domain peptide and/or nicotinamide. In the provided method, a control sample can be a blood sample (e.g., whole blood, serum or plasma sample) from a healthy subject, a blood sample from the same subject prior to SCA, or a blood sample from the same subject collected at hospital admission. An elevated blood concentration of sorbitol or taurine in the subject as compared to the control sample can include a 2-fold, 3-fold, 4-fold, 5-fold, 6-fold, 7-fold, 8-fold, 9-fold, 10-fold or higher concentration of sorbitol or taurine in the subject as compared to the control sample.

The level of taurine can be determined using any suitable reagent and method including an enzymatic assay method or UV-spectrophotometric method. In accordance with enzymatic detection of taurine, the blood sample is contacted with taurine dioxygenase (EC 1.14.11.17), divalent iron and α-ketoglutarate, and one or more of the resulting products is quantified (Matsuda & Asano (2012) *Anal. Biochem.* 427: 121-3). In some embodiments, the product is sulfite, which can be measured using, e.g., Ellman's reagent or a fluorescein-based probe (Ma, et al. (2013) *Sensor Actuat. B: Chem.* 188:1196-1200). In other embodiments, the product is 2-amino acetaldehyde, which is detected using alcohol dehydrogenase and NADH (see, e.g., WO 2011/108670). See, e.g., the Taurine Assay Kit available from BioVision Inc. (Milpitas, Calif.). UV-spectrophotometric detection of taurine can be carried out using ninhydrin (Draganov, et al. (2014) *Internat. J. Nutr. Food Sci.* 3:123-126).

Alternatively, or in addition to assessing taurine levels, blood cell sorbitol concentrations can be used to assess heart sorbitol accumulation. Sorbitol concentrations can be measured using a colorimetric assay or HPLC analysis. In colorimetric assays, sorbitol dehydrogenase catalyzes the conversion of sorbitol to fructose with the proportional development of intense color with an absorbance maximum at 560 nm. Reagents for detecting sorbitol are known in the art. See, e.g., the D-Sorbitol Colorimetric Assay Kit available from BioVision Inc. (Milpitas, Calif.). HPLC determination can be carried out using known methods (Simonzadeh & Ronsen (2012) *J. Chromatog. Sci.* 50:644-7).

This invention also provides kits containing one or more of the modified peptides, or a pharmaceutical composition containing the same, as well as (a) nicotinamide as an adjunct therapy and/or (b) one or more reagents for detecting sorbitol or taurine to guide treatment. Kits are typically provided in a suitable container (e.g., for example, a foil, plastic, or cardboard package). In certain embodiments, a kit may include one or more pharmaceutical excipients, pharmaceutical additives, and the like, as is described herein. In other embodiments, a kit may include a means for proper administration, such as, for example, graduated cups, syringes, needles, cleaning aids, and the like. In certain embodiments, a kit may include instructions for proper administration and/or preparation for proper administration. In particular embodiments, the kit may include a prefilled syringe containing a predetermined amount of one or more of the modified peptides. In another embodiment, the kit includes a prefilled syringe containing a predetermined amount of nicotinamide.

As indicated, the kit can further include reagents for detecting sorbitol and/or taurine. These reagents are of use in providing guidance for whether a subject should be treated with a modified peptide, nicotinamide and/or hypothermia; and/or for selecting the amount of modified peptide and/or nicotinamide to administer. Reagents for detecting taurine include, but are not limited to, taurine dioxygenase, divalent iron, α-ketoglutarate, Ellman's reagent, a fluorescein-based probe, alcohol dehydrogenase, NADH and ninhydrin. Reagents for detecting sorbitol include, but are not limited to, sorbitol dehydrogenase. In some embodiments, the one or more reagents for detecting taurine include taurine dioxygenase, divalent iron, α-ketoglutarate, and Ellman's reagent. In another embodiment, the one or more reagents for detecting taurine include taurine dioxygenase, divalent iron, α-ketoglutarate, and a fluorescein-based probe. In a further embodiment, the one or more reagents for detecting taurine include taurine dioxygenase, divalent iron, α-ketoglutarate, alcohol dehydrogenase and NADH. In yet a further embodiment, the one or more reagents for detecting taurine includes ninhydrin.

The following non-limiting examples are provided to further illustrate the present invention.

Example 1: TAT-PTEN9c Improves Survival after Cardiac Arrest

Two TAT-based cell permeable peptides, TAT-PTEN9c and TAT-PHLPP9c, were designed for the treatment of cardiac arrest. TAT-PTEN9c and TAT-PHLPP9c respectively target the carboxyl terminal PDZ binding motif of PTEN and PHLPPP phosphatases. TAT-PHLPP9c (YGRKKRRQRRRLPDCYDTPL; SEQ ID NO:63) and TAT-PTEN9c (YGRKKRRQRRRDQHSQITKV; SEQ ID NO:111) are 20 amino acid residue peptides, wherein 11 amino acid residues are derived from the cell-membrane transduction domain of Tat protein (YGRKKRRQRRR; SEQ ID NO:43) and the remaining 9 amino acid residues are derived from the C-terminal residues of mouse PHLPP1 (LPDCYDTPL; SEQ ID NO:8) or PTEN (DQHSQITKV; SEQ ID NO:4), respectively. Two control peptides, TAT-PTENaaa and TAT-PHLPPaaa, were also prepared. In these control peptides, the last 3 amino acid residues were mutated to alanine.

Mouse cardiomyocytes were isolated from 1-3 day old mouse pups according to known methods (Zhu, et al. (2014) *PLoS One* 9:e95622). Western blot analysis was used to determine the efficacy of a representative peptide of the invention (TAT-PTEN9c) for enhancing Akt phosphorylation in mouse cardiomyocytes exposed to oxidant ($H_2O_2$) or IGF-1. C57BL6 mice were subjected to an established potassium-induced 8-minute SCA protocol (Li, et al. (2015) *Am. J. Physiol. Heart Circ. Physiol.* 308:H1414-22). Mean arterial blood pressure (MAP), end-tidal $CO_2$ ($EtCO_2$), body temperature and electrocardiogram (ECG) were recorded until hours after successful cardiopulmonary resuscitation (CPR). TAT-PTEN9c (7.5 mg/kg) or saline was given intravenously (IV) immediately after ROSC. A mouse survival curve was generated by Kaplan-Meyer analysis. IV administration of TAT-GFP was used to measure the kinetics of heart and brain tissue TAT protein delivery.

Figure 1B:
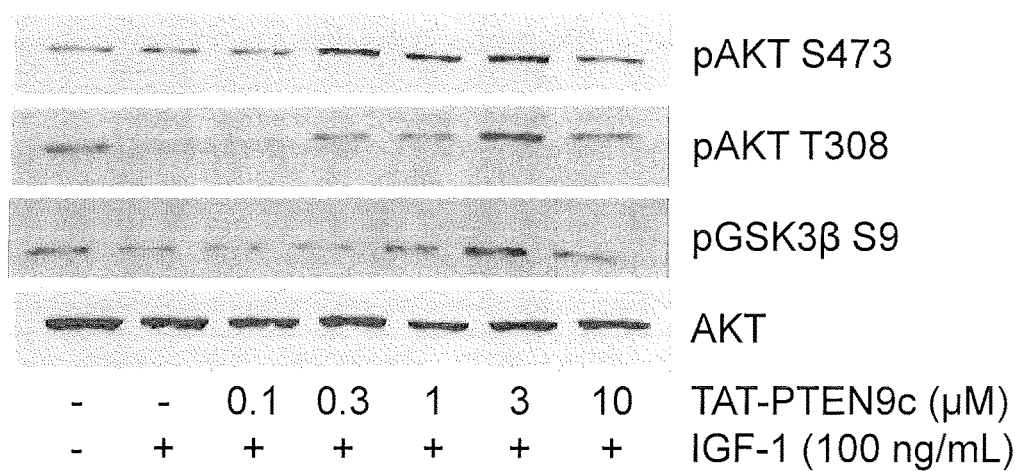
Figure 1C:
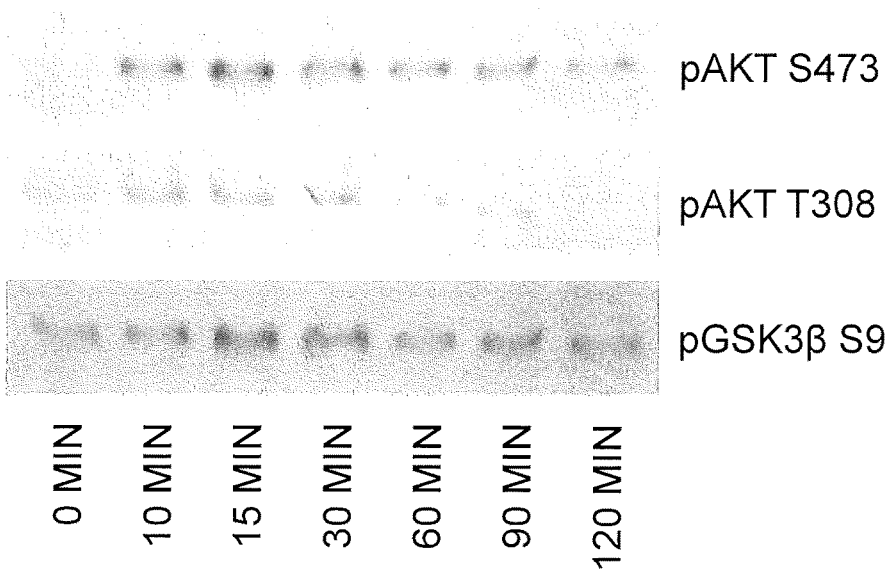
Figure 2:
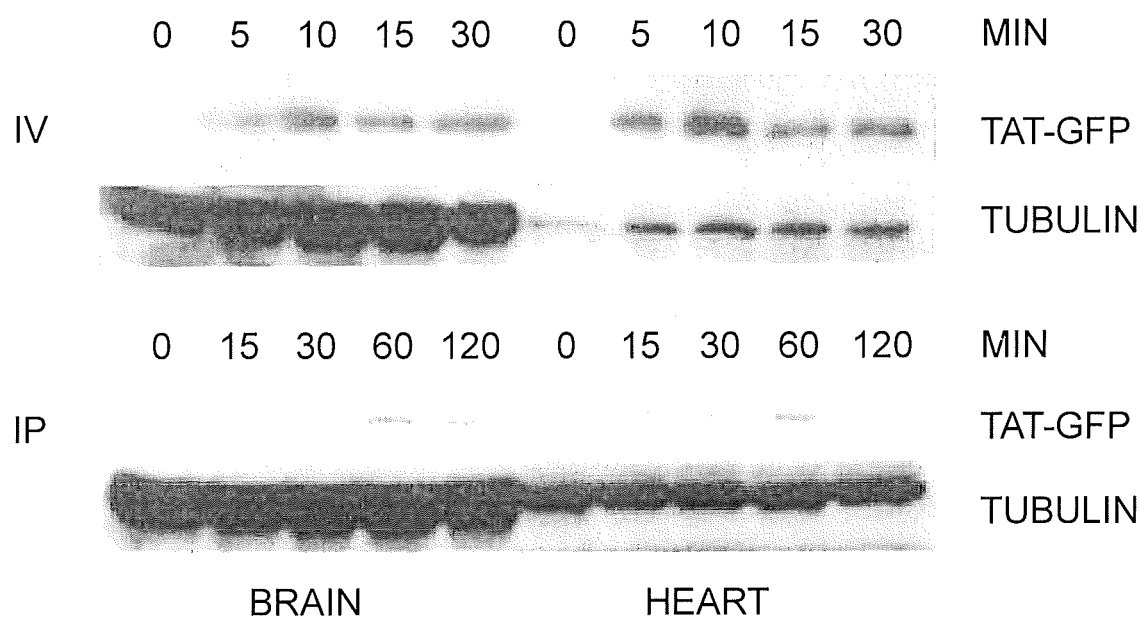
FIG. 2 shows that TAT-GFP transduction in heart and brain is diffuse and occurs within 5 minutes after IV administration, whereas TAT-GFP transduction was evident in brain and heart with 15-30 minutes after IP administration.
Figure 3:
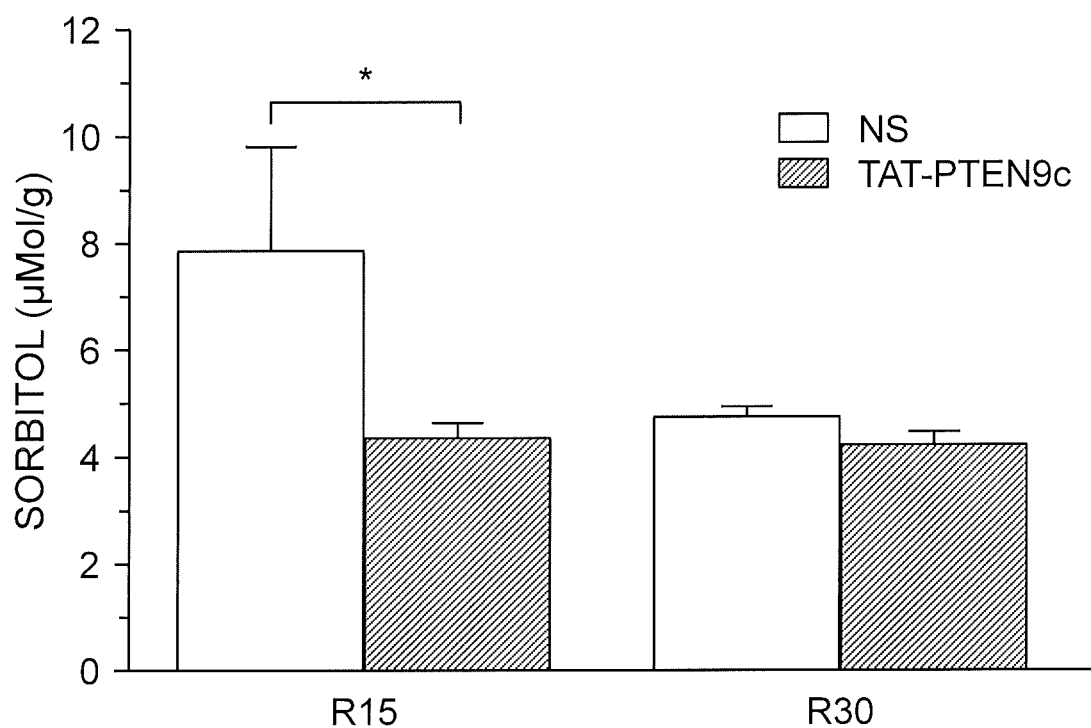
FIG. 3 shows that brain tissue from mice treated with TAT-PTEN9c peptide exhibited significantly decreased sorbitol content at 15 (R15) and 30 (R30) minutes after ROSC as compared to saline control (NS).
Figure 4:
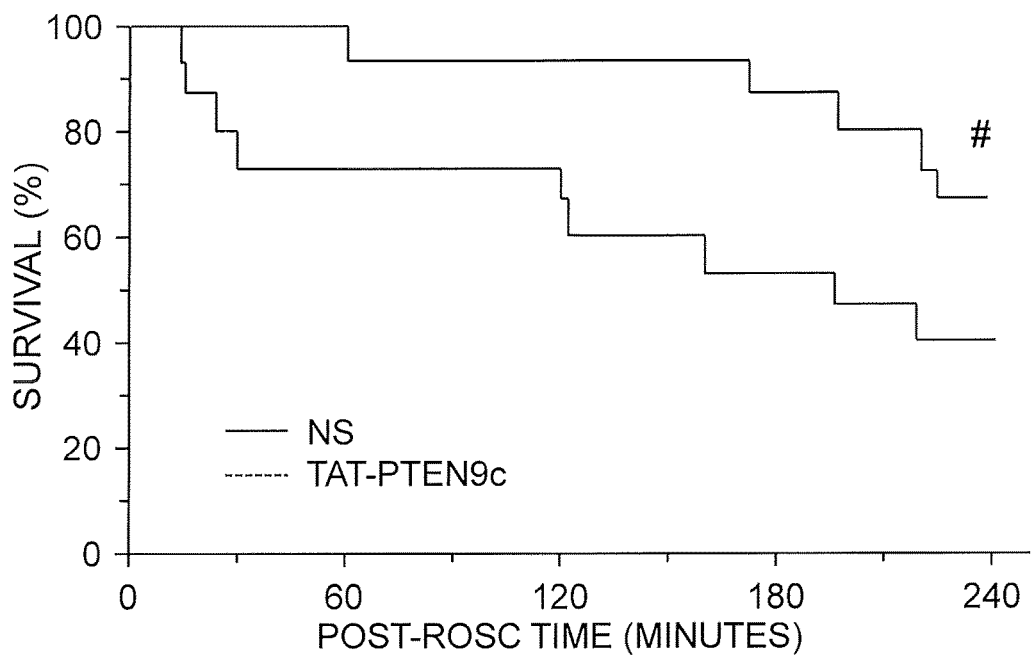
FIG. 4 shows that the administration of TAT-PTEN9c immediately after ROSC significantly improves survival of mice after cardiac arrest as compared to saline control (NS).
Figure 5:
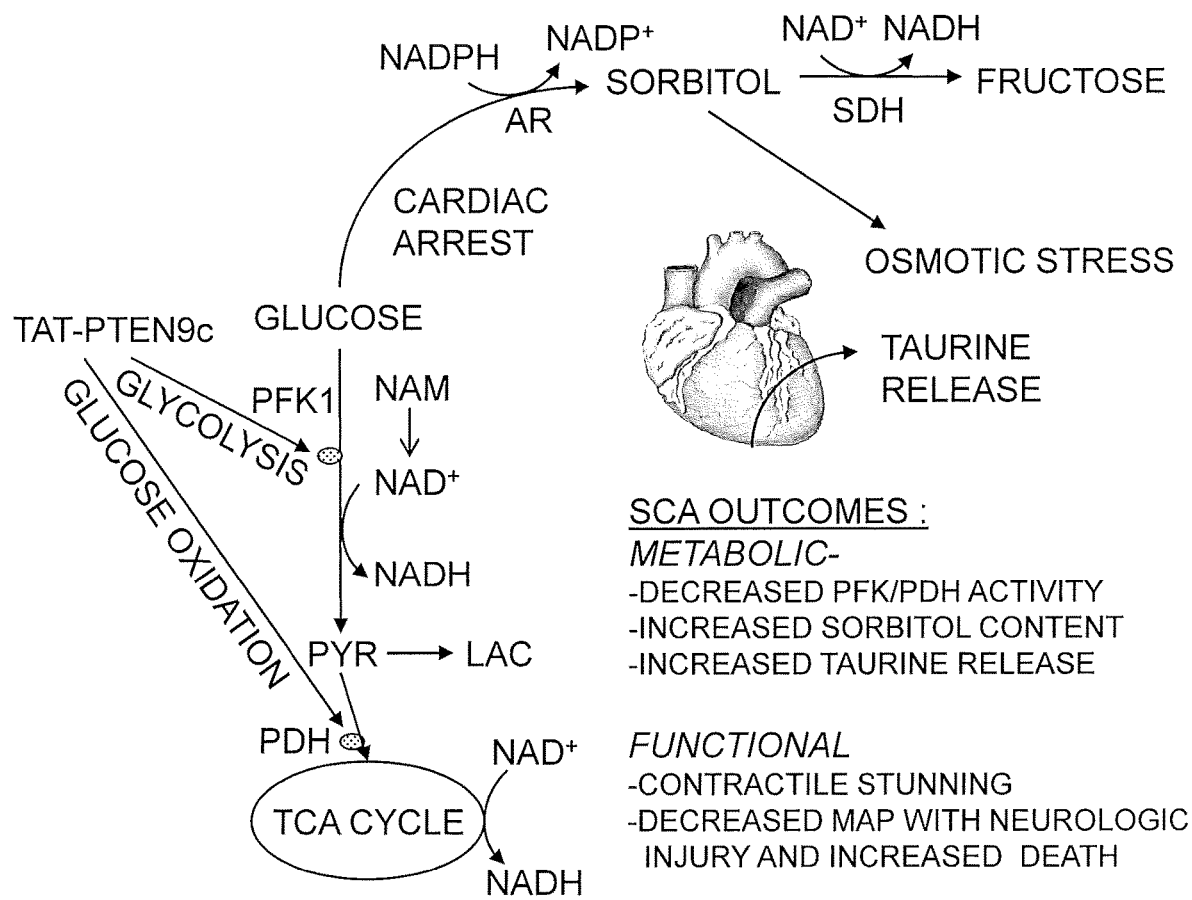
FIG. 5 shows that the heart is the primary source of taurine and the blood taurine concentrations positively correlate with heart sorbitol concentrations.

The foregoing experiments showed that TAT-PTEN9c rapidly enhanced Akt activation in mouse cardiomyocytes in a concentration-dependent manner (FIGS. 1A-1C). Western blot and immunohistochemistry showed that TAT protein transduction in heart and brain was diffuse and occurred within 5 minutes after IV administration (FIG. 2). Treated mice had brain tissues with significantly decreased sorbitol content, suggesting improved metabolic recovery and glucose utilization (FIG. 3). In addition, administration of TAT-PTEN9c immediately after ROSC improved MAP and $EtCO_2$ (Table 4) and significantly improved survival of mice after cardiac arrest (FIG. 4).

TABLE 4

| | Parameter | Control (n = 15) | TAT-PTEN9c (n = 15) |
|---|---|---|---|
| Baseline | Weight (g) | 27.7 ± 1.9 | 29.4 ± 2.4 |
| | MAP (mmHg) | 83.1 ± 10.2 | 81.5 ± 9.2 |
| | $EtCO_2$ (mmHg) | 42.1 ± 2.0 | 40.3 ± 3.0 |
| | Heart Rate (bpm) | 303.9 ± 51.2 | 274.8 ± 30.7 |
| Resuscitation | CPR time to ROSC (seconds) | 135.1 ± 16.8 | 145.3 ± 23.2 |
| | CC rate (bpm) | 348.5 ± 16.1 | 354.5 ± 11.5 |
| | DBP (mmHg) | 21.9 ± 3.5 | 23.7 ± 3.6 |
| | $EtCO_2$ (mmHg) | 23.9 ± 1.6 | 23.5 ± 3.6 |
| 240 minutes | MAP (mmHg) | 49.0 ± 14 | 52.7 ± 9.3 |
| | $EtCO_2$ (mmHg) | 34.7 ± 0.5 | 36.2 ± 6.7 |
| | Heart Rate (bpm) | 527.8 ± 38.3 | 502.0 ± 62.2 |
| | Survival, n (%) | 6 (40) | 10 (66.7) |

Example 2: TAT-PTEN9c Administered After ROSC Provides Benefit

To determine timing of modified peptide administration, TAT-PTEN9c was administrated during CPR or after ROSC. C57BL6 mice were subjected to an established potassium-induced 8-minute SCA protocol (Li, et al. (2015) *Am. J. Physiol. Heart Circ. Physiol.* 308:H1414-22). Mean arterial blood pressure (MAP) was recorded until 4 hours after successful CPR. TAT-PTEN9c (7.5 mg/kg) or saline (NS) was given intravenously (IV) during CPR and immediately after ROSC.

This analysis indicated that TAT-PTEN9c administered during CPR had no improvement on resuscitation rate, whereas TAT-PTEN9c administered after ROSC significantly improved MAP at 30 minutes (65.2±1.1 mmHg vs. 57.5±1.0 mmHg in NS) and 4 hours after ROSC (49.9±0.7 mmHg vs. 43.7±3.5 mmHg in NS, $p<0.05$).

Example 3: Combination Treatment of Nicotinamide and TAT-PTEN9c

The benefit of co-administration of nicotinamide (NAM) with TAT-PTEN9c was evaluated. C57BL6 mice were subjected to an established potassium-induced 8-minute SCA protocol. Nicotinamide (Vitamin B3) was administered during CPR and TAT-PTEN9c was administered after ROSC with about a 12 minute down time for each group.

For the control group (normal saline; n=3 ROSC), all mice survived for less than 10 minutes. For the nicotinamide only group (NAM, n=5 ROSC), all mice survived for less than 1 hour. For the NAM and TAT-PTEN9c group (n=7), all mice survived between 1-4 hours.

Example 4: Metabolic Markers Predict Heart Function and Survival after Sudden Cardiac Arrest Metabolism alteration and energy production are critical outcomes following SCA. Using a mouse model of SCA (Li, et al. (2015) *Am. J. Physiol. Heart Circ. Physiol.* 308: H1414-22), several metabolic compounds were identified as diagnostic markers for use in guiding the selection of treatment protocols (e.g., active cooling, therapeutic hypothermia, or modified PDZ binding domain peptide therapies).

Nicotinamide adenine dinucleotide (NAD), a critical cofactor for glucose utilization, falls rapidly within minutes of ischemia. The loss of NAD impairs glucose metabolism resulting in diversion of glucose via the polyl pathway to sorbitol. The increased accumulation of sorbitol alters tissue osmolarity and promotes the release of taurine into blood as a compensatory response to the osmotic stress created by sorbitol accumulation. The heart is the primary source of taurine and the blood taurine concentrations positively correlate with heart sorbitol concentrations. See FIG. 6. It has now been observed that high blood concentrations of sorbitol or taurine are associated with poor survival of SCA mice and SCA patients. In a mouse model of SCA, blood taurine concentrations were reduced by both active cooling during CPR as well as the administration of VO-OHpic. Thus, high blood concentrations of sorbitol or taurine reflect the metabolic recovery state of the heart during SCA and serve as diagnostic markers guiding treatment and predicting outcomes after SCA.

What is claimed is:

1. A modified peptide comprising a PDZ binding domain consisting of SEQ ID NO:2 or a PDK1 interacting fragment consisting of SEQ ID NO:3 and
   (a) between one and 50 additional non-native amino acid residues,
   (b) introduction of one or more nonhydrolyzable bonds, or
   (c) a combination of (a) and (b).

2. The modified peptide of claim 1, wherein the additional non-native amino acid residues comprise a cell-penetrating peptide.

3. A modified peptide comprising the amino acid sequence of SEQ ID NO:63-110 or 159-206.

4. A pharmaceutical composition comprising the modified peptide of claim 1 and a pharmaceutically acceptable carrier.

5. The pharmaceutical composition of claim 4, further comprising nicotinamide.

6. A pharmaceutical composition comprising
   (i) a modified peptide comprising a PDZ binding domain consisting of SEQ ID NO:2 and
      (a) between one and 50 additional non-native amino acid residues,
      (b) introduction of one or more nonhydrolyzable bonds, or
      (c) a combination of (a) and (b);
   (ii) a modified peptide comprising a PDK1 interacting fragment consisting of SEQ ID NO:3 and
      (a) between one and 50 additional non-native amino acid residues,
      (b) introduction of one or more nonhydrolyzable bonds, or
      (c) a combination of (a) and (b); and
   (iii) a pharmaceutically acceptable carrier.

7. The pharmaceutical composition of claim 6, further comprising nicotinamide.

8. A kit comprising
   (i) one or a combination of
      a modified peptide comprising a PDZ binding domain consisting of SEQ ID NO:2 and
         (a) between one and 50 additional non-native amino acid residues,
         (b) introduction of one or more nonhydrolyzable bonds, or
         (c) a combination of (a) and (b); or
      a modified peptide comprising a PDK1 interacting fragment consisting of SEQ ID NO:3 and
         (a) between one and 50 additional non-native amino acid residues,
         (b) introduction of one or more nonhydrolyzable bonds; and
   (ii) nicotinamide, one or more reagents for detecting sorbitol, one or more reagents for detecting taurine, or a combination thereof.

9. The kit of claim 8, wherein the additional non-native amino acid residues comprise a cell-penetrating peptide.

* * * * *

UNITED STATES PATENT AND TRADEMARK OFFICE
CERTIFICATE OF CORRECTION

PATENT NO. : 10,688,153 B2  
APPLICATION NO. : 15/769132  
DATED : June 23, 2020  
INVENTOR(S) : Terry Vanden Hoek, Xiangdong Zhu and Jing Li Page 1 of 1

It is certified that error appears in the above-identified patent and that said Letters Patent is hereby corrected as shown below:

On the Title Page

At (73) Assignee: please correct Urbaba, IL (US) to Urbana, IL (US)

Signed and Sealed this  
First Day of December, 2020

Andrei Iancu  
*Director of the United States Patent and Trademark Office*